US007119112B2

(12) United States Patent
McNaughton-Smith et al.

(10) Patent No.: US 7,119,112 B2
(45) **Date of Patent: *Oct. 10, 2006**

(54) SULFONAMIDES AS POTASSIUM CHANNEL BLOCKERS

(75) Inventors: Grant A. McNaughton-Smith, Morrisville, NC (US); Aimee D. Reed, Willoughby, OH (US); Robert N. Atkinson, Raleigh, NC (US)

(73) Assignee: ICAgen, Inc., Durham, NC (US)

( * ) Notice: Subject to any disclaimer, the term of this patent is extended or adjusted under 35 U.S.C. 154(b) by 24 days.

This patent is subject to a terminal disclaimer.

(21) Appl. No.: 10/641,686

(22) Filed: Aug. 14, 2003

(65) Prior Publication Data

Related U.S. Application Data

(63) Continuation-in-part of application No. 10/376,878, filed on Feb. 28, 2003.

(60) Provisional application No. 60/403,898, filed on Aug. 15, 2002, provisional application No. 60/360,644, filed on Feb. 28, 2002.

(51) Int. Cl.
*A61K 31/425* (2006.01)
*C07D 275/02* (2006.01)

(52) U.S. Cl. ...................... 514/365; 514/374; 514/364; 548/214; 548/235; 548/131; 549/491

(58) Field of Classification Search ................ 548/214, 548/235, 131; 549/491; 574/365, 374, 364, 574/461
See application file for complete search history.

(56) References Cited

U.S. PATENT DOCUMENTS

| | | | |
|---|---|---|---|
| 5,652,236 A | 7/1997 | Krauss | |
| 5,925,342 A | 7/1999 | Adorante et al. | |
| 6,172,054 B1 | 1/2001 | Clark | |
| 6,172,109 B1 | 1/2001 | Zinke et al. | |
| 2004/0029771 A1* | 2/2004 | Rigdon et al. | 514/1 |

FOREIGN PATENT DOCUMENTS

WO WO 99/32101 A1 7/1999

OTHER PUBLICATIONS

Supuran et al., 1998, CAS:129:132963.*

Do et al., "Chloride Secretion by Bovine Ciliary Epithelium: a Model of Aquenos Humor Formation", *Investigative Ophthalmology & Visual Science* 41:7: 1853-1860 (2000).

Ishii et al., "A human intermediate conductance calcium-activated potassium channel", *Proc. Natl. Acad. Sci. USA* 94: 11651-11656 (1997).

Jensen et al., "Characterization of the cloned human intermediate-conductance $Ca^{2+}$-activated $K^+$channel", *The American Physiological Society* C848-C856 (1998).

Joiner et al., "hSK4, a member of a novel subfamily of calcium-activated potassium channels", *Proc. Natl. Acad. Sci. USA* 94: 11013-11018 (1997).

Logsdon et al., "A Novel Gene, hKCa4, Encodes the Calcium-activated Potassium Channel in Human T Lymphocytes", *The Journal of Biological Chemistry* 272:52: 32723-32726 (1997).

Neylon et al., "Molecular Cloning and Characterization of the Intermediate-Conductance $Ca^{2+}$-Activated $K^+$Channel in Vascular Smooth Muscle: Relationship Between $K_{ca}$ Channel Diversity and Smooth Muscle Cell Function", *Department of Neurobiology, Duke University Medical Center UltraRapid Communication*, 1-11 (1999).

Serke et al., "Effect of Pilocarpine 4% in Combination with Latanoprost 0.005% or 8-iso Prostaglandin $E_2$ 0.1% on Intraocular Pressure in Laser-induced Glaucomatous Monkey Eyes", *Journal of Glaucoma* 10: 215-219 (2001).

Stumpff et al., "Regulation of Trabecular Meshwork Contractility", *Ophthalmologica* 214: 33-53 (2000).

Stumpff et al., "Stimulation of Maxi-K Channels in Trabecular Meshwork by Tyrosine Kinase Inhibitors", *Inv. Ophth. & Vis. Sci.* 40:7: 1404-1417 (1999).

Vandorpe et al., "cDNA Cloning and Functional Characterization of the Mouse $Ca^{2+}$-gated $K^+$Channel, mIK1", *The Journal of Biochemistry* 273:34: 21542-21553 (1998).

Vogalis et al., "An intermediate conductance $K^+$channel in the cell membrane of mouse intestinal smooth muscle", *Biochimica et Biophysica Acta* 1371: 309-316 (1998).

Wang et al., "Effect of Latanoprost or 8-iso Prostaglandin $E_2$ Alone and in Combination on Intraocular Pressure in Glaucomatous Monkey Eyes", *Arch Ophthalmol* 118: 74-77 (2000).

Warth et al., "Molecular and functional characterization of the small $Ca^{2+}$-regulated K+ channel (rSK4) of colonic cryps", *Eur. J. Physiol.* 438: 437-444 (1999).

Weiderholt et al., "The Regulation of Trabecular Meshwork and Ciliary Muscle Contractility", *Progress in Retinal and Eye Research* 19:3: 271-295 (2000).

Wiederholt et al., "Effect of Diuretics, Channel Modulators and Signal Interceptors on Contractility of the Trabecular Meshwork", *Ophthalmologica* 211: 153-160 (1997).

Zhang et al., "Three different $Cl^-$channels in the bovine ciliary epithelium activated by hypotonic stress", *Journal of Physiology* 499:2: 379-389 (1997).

* cited by examiner

*Primary Examiner*—Kamal A. Saeed
*Assistant Examiner*—Robert Shiao
(74) *Attorney, Agent, or Firm*—Townsend and Townsend and Crew LLP

(57) ABSTRACT

Compounds, compositions and methods are provided which are useful in the treatment of diseases through the modulation of potassium ion flux through voltage-dependent potassium channels. More particularly, the invention provides sulfonamides, and compositions and methods utilizing sulfonamides that are useful in the treatment of diseases by blocking potassium channels associated with the onset or recurrence of the indicated conditions. Exemplary diseases treatable with the compounds, compositions and methods of the invention include sickle cell disease and glaucoma.

8 Claims, 8 Drawing Sheets

| | | | | |
|---|---|---|---|---|
| 1 |  | | 13 |  |
| 2 |  | | 14 |  |
| 3 |  | | 15 |  |
| 4 |  | | 16 |  |
| 5 |  | | 17 |  |
| 6 |  | | 18 |  |
| 7 |  | | 19 |  |
| 8 |  | | 20 |  |
| 9 |  | | 21 |  |
| 10 |  | | 22 |  |
| 11 |  | | 23 |  |
| 12 |  | | 24 |  |

| | | | | |
|---|---|---|---|---|
| 25 |  | | 37 |  |
| 26 |  | | 38 |  |
| 27 |  | | 39 |  |
| 28 |  | | 40 |  |
| 29 |  | | 41 |  |
| 30 |  | | 42 |  |
| 31 |  | | 43 |  |
| 32 |  | | 44 |  |
| 33 |  | | 45 |  |
| 34 |  | | 46 |  |
| 35 |  | | 47 |  |
| 36 |  | | 48 |  |

| | | | | |
|---|---|---|---|---|
| 49 |  | | 61 |  |
| 50 |  | | 62 |  |
| 51 |  | | 63 |  |
| 52 |  | | 64 |  |
| 53 |  | | 65 |  |
| 54 |  | | 66 |  |
| 55 |  | | 67 |  |
| 56 |  | | 68 |  |
| 57 |  | | 69 |  |
| 58 |  | | 70 |  |
| 59 |  | | 71 |  |
| 60 |  | | 72 |  |

| | | | | |
|---|---|---|---|---|
| 73 |  | | 85 |  |
| 74 |  | | 86 |  |
| 75 |  | | 87 |  |
| 76 |  | | 88 |  |
| 77 |  | | 89 |  |
| 78 |  | | 90 |  |
| 79 |  | | 91 |  |
| 80 |  | | 92 |  |
| 81 |  | | 93 |  |
| 82 |  | | 94 |  |
| 83 |  | | 95 |  |
| 84 |  | | 96 |  |

| | | | | |
|---|---|---|---|---|
| 97 |  | | 109 |  |
| 98 |  | | 110 |  |
| 99 |  | | 111 |  |
| 100 |  | | 112 |  |
| 101 |  | | 113 |  |
| 102 |  | | 114 |  |
| 103 |  | | 115 |  |
| 104 |  | | 116 |  |
| 105 |  | | 117 |  |
| 106 |  | | 118 |  |
| 107 |  | | 119 |  |
| 108 |  | | 120 |  |

| | | | | |
|---|---|---|---|---|
| 121 |  | | 133 |  |
| 122 |  | | 134 |  |
| 123 |  | | 135 |  |
| 124 |  | | 136 |  |
| 125 |  | | 137 |  |
| 126 |  | | 138 |  |
| 127 |  | | 139 |  |
| 128 |  | | 140 |  |
| 129 |  | | 141 |  |
| 130 |  | | 142 |  |
| 131 |  | | 143 |  |
| 132 |  | | 144 |  |

| | | | | |
|---|---|---|---|---|
| 145 |  | | 157 |  |
| 146 |  | | 158 |  |
| 147 |  | | 159 |  |
| 148 |  | | 160 |  |
| 149 |  | | 161 |  |
| 150 |  | | 162 |  |
| 151 |  | | 163 |  |
| 152 |  | | 164 |  |
| 153 |  | | 165 |  |
| 154 |  | | 166 |  |
| 155 |  | | 167 |  |
| 156 |  | | 168 |  |

| | | | | |
|---|---|---|---|---|
| 169 |  | | | |
| 170 |  | | | |
| 171 |  | | | |
| 172 |  | | | |
| 173 |  | | | |
| 174 |  | | | |
| 175 |  | | | |

SULFONAMIDES AS POTASSIUM CHANNEL BLOCKERS

CROSS REFERENCE TO RELATED APPLICATIONS

The present application claims the benefit of U.S. Ser. No. 60/403,898, filed Aug. 15, 2002, and is a continuation-in-part of U.S. Ser. No. 10/376,878, filed Feb. 28, 2003, which claims the benefit of U.S. Ser. No. 60/360,644, filed Feb. 28, 2002.

FIELD OF THE INVENTION

This invention relates to the use of sulfonamides as potassium channel blockers and to the treatment of diseases modulated by potassium channels. Additionally, this invention relates to sulfonamide compounds that are useful as potassium channel blockers.

BACKGROUND OF THE INVENTION

Ion channels are cellular proteins that regulate the flow of ions, including calcium, potassium, sodium and chloride into and out of cells. These channels are present in all human cells and affect such physiological processes as nerve transmission, muscle contraction, cellular secretion, regulation of heartbeat, dilation of arteries, release of insulin, and regulation of renal electrolyte transport. Among the ion channels, potassium channels are the most ubiquitous and diverse, being found in a variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into at least 8 families, based on predicted structural and functional similarities (Wei et al., *Neuropharmacology* 35(7): 805–829 (1997)). Three of these families (Kv, eag-related, and KQT) share a common motif of six transmembrane domains and are primarily gated by voltage. Two other families/ also contain this motif but are gated by cyclic nucleotides (CNG) and calcium (small conductance and intermediate conductance potassium channels), respectively. The small conductance and intermediate conductance, calcium activated potassium channels comprise a family of calcium activated potassium channels gated solely by calcium, with a unit conductance of 2-20 and 20-85 pS, respectively. Macroscopic and unitary intermediate conductance, calcium activated potassium channel currents show inward rectification (see, e.g., Ishii et al., *Proc. Natl. Acad. Sci USA* 94: 11651–11656 (1997). The three other families of potassium channel alpha subunits have distinct patterns of transmembrane domains. Slo family potassium channels, or BK channels have seven transmembrane domains (Meera et al., *Proc. Natl. Acad. Sci. U.S.A.* 94(25): 14066–71 (1997)) and are gated by both voltage and calcium or pH (Schreiber et al., *J. Biol. Chem.* 273: 3509–16 (1998)). Another family, the inward rectifier potassium channels (Kir), belongs to a structural family containing two transmembrane domains, and an eighth functionally diverse family (TP, or "two-pore") contains two tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels made from Kv, KQT and Slo or BK subunits have often been found to contain additional, structurally distinct auxiliary, or beta, subunits. These subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493: 625–633 (1996); Shi et al., *Neuron* 16(4): 843–852 (1996)). In another example, the KQT family beta subunit, minK, primarily changes activation kinetics (Sanguinetti et al., *Nature* 384: 80–83 (1996)).

The intermediate conductance, calcium activated potassium channel is also called SK4, KCa4, IKCa, SMIK, and Gardos. Intermediate conductance, calcium activated potassium channels have been previously described in the literature by their electrophysiology. For example, the Gardos channel, a well-known intermediate conductance, calcium activated potassium channel, is opened by submicromolar concentrations of internal calcium and has a rectifying unit conductance, ranging from 50 pS at −120 mV to 13 pS at 120 mV (symmetrical 120 mM K+; Christopherson, *J. Membrane Biol.* 119: 75–83 (1991)). Intermediate conductance, calcium activated potassium channels are blocked by charybdotoxin (CTX) but not the structurally related peptide iberiotoxin (IBX), both of which block BK channels (Brugnara et al., *J. Membr. Biol.* 147: 71–82 (1995)). Intermediate conductance, calcium activated potassium channels are also blocked by maurotoxin. Apamin, a potent blocker of certain native (Vincent et al., *J. Biochem.* 14: 2521 (1975); Blatz & Magleby, *Nature* 323: 718–720 (1986)) and cloned SK channels does not block intermediate conductance, calcium activated potassium channels (de-Allie et al., *Br. J. Pharm.* 117: 479–487 (1996)). The Gardos channel is also blocked by some imidazole compounds, such as clotrimazole, but not ketoconazole (Brugnara et al, *J. Clin. Invest.,* 92: 520–526 (1993)). Intermediate conductance, calcium activated potassium channels can therefore be distinguished from the other calcium activated potassium channels by their biophysical and pharmacological profiles. Intermediate conductance, calcium activated potassium channels from different tissues have been reported to possess a wide range of unit conductance values.

Human intermediate conductance, calcium activated potassium channels have been cloned and characterized (see, e.g., Ishii et al., *Proc. Natl. Acad. Sci. USA* 94: 11651–11656 (1997); Genbank Accession No. AF0225150; Joiner et al., *Proc. Natl. Acad. Sci. USA* 94: 11013–11018 (1997); Genbank Accession No. AF000972; Lodsdon et al., *J. Biol. Chem.* 272: 32723–32726 (1997); Genbank Accession No. AF022797; and Jensen et al., *Am. J. Physiol.* 275: C848–856 (1998); see also WO 98/11139; WO 99/03882; WO 99/25347; and WO 00/12711). Non-human intermediate conductance, calcium activated potassium channels have also been cloned, e.g., from mouse and rats (see, e.g., Vandorpe et al., *J. Biol. Chem.* 273: 21542–21553 (1998); Genbank Accession No. NM_032397; Warth et al., *Pflugers Arch.* 438: 437–444 (1999); Genbank Accession No. AJ133438; and Neylon et al., *Circ. Res.* (online)85: E33–E43 (1999); Genbank Accession No. AF190458). The gene for the intermediate conductance, calcium activated potassium channels is named KCNN4 and it is located on chromosome 19q13.2 (Ghanshani et al., *Genomics* 51: 160–161 (1998)).

The intermediate conductance, calcium activated potassium channel is implicated in the regulation of mammalian cell proliferation (see, for example, Wulff et al., *Proc. Nat. Acad. Sci. USA* 97: 8151–8156 (2000)) and the dehydration and sickling of erythrocytes in sickle cell disease. Sickle cell disease has been recognized within West Africa for several centuries. Sickle cell anemia and the existence of sickle hemoglobin (Hb S) was the first genetic disease to be understood at the molecular level. It is recognized today as the morphological and clinical result of a glycine to valine substitution at the No. 6 position of the beta-globin chain (Ingram, *Nature* 178: 792–794 (1956)). The origin of the amino acid change and of the disease state is the consequence of a single nucleotide substitution (Marotta et al., *J. Biol. Chem.* 252: 5040–5053 (1977)).

Normal erythrocytes are comprised of approximately 70% water. Water crosses a normal erythrocyte membrane in milliseconds. Loss of cell water causes an exponential increase in cytoplasmic viscosity as the mean cell hemoglobin concentration (MCHC) rises above about 32 g/dl. Since cytoplasmic viscosity is a major determinate of erythrocyte deformability and sickling, the dehydration of the erythrocyte has substantial rheological and pathological consequences. Regulation of erythrocyte dehydration is recognized as an important therapeutic approach for treating sickle cell disease. Since cell water follows any osmotic change in intracellular ion concentration, maintaining the red cell's potassium concentration is of particular importance (Stuart et al., *Brit J. Haematol.* 69: 1–4 (1988)).

An approach towards therapeutically treating dehydrated sickle cells involves altering erythrocyte potassium flux by targeting a calcium-dependent potassium channel. This calcium activated potassium channel is also referred to as the Gardos channel (Brugnara et al, *J. Clin. Invest.* 92: 520–526 (1993)). Recently, a cloned human intermediate conductance, calcium activated potassium channel, was shown to be substantially similar to the Gardos channel in terms of both its biophysical and pharmacological properties (Ishii et al., *Proc. Natl. Acad. Sci. USA* 94: 11651–11656 (1997)).

In vitro studies have shown that clotrimazole, an imidazole-containing antimycotic agent, blocks $Ca^{2+}$-activated $K^+$ flux and cell dehydration in sickle erythrocytes (Brugnara et al., *J. Clin. Invest.* 92: 520–526 (1993)). Studies in a transgenic mouse model for sickle cell disease, SAD-1 mouse (Trudel et al., *EMBO J.* 11: 3157–3165 (1991)), show that oral administration of clotrimazole leads to inhibition of the red cell Gardos channel, increased red cell $K^+$ content, a decreased mean corpuscular hemoglobin concentration (MCHC) and decreased cell density (De Franceschi et al., *J. Clin. Invest.* 93: 1670–1676 (1994)). Moreover, therapy with oral clotrimazole induces inhibition of the Gardos channel and reduces erythrocyte dehydration in patients with sickle cell disease (Brugnara et al., *J. Clin. Invest.* 97: 1227–1234 (1996)). Other antimycotic agents, which inhibit the Gardos channel in vitro, include miconazole, econazole, butoconazole, oxiconazole and sulconazole (U.S. Pat. No. 5,273,992 to Brugnara et al.). All of these compounds contain an imidazole-like ring. i.e., a heteroaryl ring containing two or more nitrogens.

Although of demonstrable efficacy, the imidazole-based Gardos channel inhibitors that have been explored to date are hampered by several shortcomings including a well-documented potential for hepatotoxicity. This toxicity is exacerbated by the inhibitors' low potencies, non-specific interactions with potassium channels other than the Gardos channel and low bioavailabilities, each of which motivate for the administration of higher and more frequent dosages of the inhibitors.

Glaucoma is a disease characterized by increased intraocular pressure. Increased intraocular pressure is associated with many diseases including, but not limited to, primary open-angle glaucoma, normal tension glaucoma, angle-closure glaucoma, acute glaucoma, pigmentary glaucoma, neovascular glaucoma, or trauma related glaucoma, Sturge-Weber syndrome, uveitis, and exfoliation syndrome.

Currently, there are a variety of drugs available that employ different mechanisms to lower intraocular pressure, e.g., timolol, betaxolol, levobunolol, acetazolamide, methazolamide, dichlorphenamide, dorzolamide, brinzolamide, latanoprost, brimonidine, and rescula (see, e.g., U.S. Pat. Nos. 6,172,054, 6,172,109, and 5,652,236). Miotics, beta blockers, alpha-2 agonists, carbonic anhydrase inhibitors, beta adrenergic blockers, prostaglandins and docosanoid are all currently used alone or in combination to treat glaucoma. Miotics and prostaglandins are believed to lower intraocular pressure by increasing drainage of the intraocular fluid, while beta blockers, alpha-2 agonists and carbonic anhydrase are believed to lower intraocular pressure by decreasing production of intraocular fluid thereby reducing the flow of fluid into the eye. All are characterized by side effects ranging from red eye and blurring of vision to decreased blood pressure and breathing difficulties.

In view of the above-described shortcomings of currently known methods of treating diseases in which the intermediate conductance, calcium activated potassium channel is implicated, a substantial advance in the treatment of diseases related to potassium flux is expected from the discovery of new intermediate conductance, calcium activated potassium channel inhibitors. The present invention provides a new genus of such ion channel inhibitors based on a sulfonamide-containing scaffold.

SUMMARY OF THE INVENTION

The present invention provides compounds capable of inhibiting the intermediate conductance, calcium activated potassium channel thus providing a novel approach towards the treatment and/or prevention of diseases in which said channel is implicated, as described below. Compounds capable of inhibiting the intermediate conductance, calcium activated potassium channel are highly desirable, and are an object of the present invention.

Thus, in one aspect, the present invention provides compounds according to Formula I:

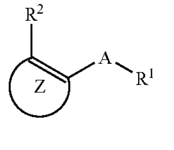

(I)

in which the ring system Z is selected from substituted or unsubstituted aryl, substituted or unsubstituted heteroaryl, substituted or unsubstituted carbocycle, or substituted or unsubstituted heterocycloalkyl. The symbol A represents $-NHS(O)_2-$, $-S(O)_2NH-$, $-C(R^4R^5)S(O)_n-$, $-S(O)_nC(R^4R^5)-$, $-C(R^4R^5)NHS(O)_n-$, $-S(O)_nNHC(R^4R^5)-$, $-C(R^4R^5)S(O)_nNH-$, or $-HNS(O)_nC$ ($R^4R^5$)—. The symbol $R^1$ represents a substituted or unsubstituted aryl group, a substituted or unsubstituted heteroaryl group, a substituted or unsubstituted carbocycle, or substituted or unsubstituted heterocycloalkyl. The symbol $R^2$ represents $COOR^3$, substituted or unsubstituted 2-furan, substituted or unsubstituted 2-thiazole or

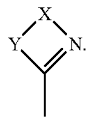

The symbol $R^3$ represents a substituted or unsubstituted $C_1$–$C_4$ alkyl group, e.g, methyl, ethyl, or —$CF_3$. X represents —N═N—, —N═C($R^4$)—, —C($R^4$)═N—, —C($R^4R^5$)—C($R^4R^5$)— or —C($R^4$)═C($R^5$)—, in which $R^4$ and $R^5$ independently represent hydrogen, halogen, substituted and unsubstituted lower alkyl, —$OR^6$ or —$CF_3$. The symbol Y represents O, $NR^{11}$ or S, in which $R^{11}$ is —H, lower alkyl or —$CF_3$. The symbol $R^6$ represents a member selected from hydrogen, substituted or unsubstituted lower alkyl or —$CF_3$.

In another aspect, the present invention provides pharmaceutical compositions comprising a pharmaceutically acceptable excipient and a compound of Formula I.

Controlling diseases (e.g., sickle cell disease, glaucoma, rheumatoid arthritis, uveitis, diseases characterized by abnormal cell proliferation, among others) via altering cellular ionic fluxes of cells affected by a disease is a powerful therapeutic approach. Moreover, basic understanding of the role of cellular ionic fluxes in both disease processes and normal physiology promises to provide new therapeutic modalities, regimens and agents. Compounds that alter cellular ion fluxes, particularly those that inhibit potassium flux, are highly desirable as both drugs and as probes for elucidating the basic mechanisms underlying these ion fluxes. Similarly, methods utilizing these compounds in basic research and in therapeutic applications are valuable tools in the arsenal of both the researcher and clinician. Therefore such compounds and methods are also an object of the present invention.

Thus, in a third aspect, the present invention provides a method of inhibiting potassium flux of a cell. The method comprises contacting a cell with an amount of a compound according to Formula I, effective to inhibit the potassium flux.

An important therapeutic pathway for treatment of sickle cell disease is preventing or retarding the dehydration of erythrocytes by manipulating the cellular ion fluxes of erythrocytes. Thus, in another aspect, the invention provides a method for reducing erythrocyte dehydration. The method comprises contacting an erythrocyte with an amount of a compound according to Formula I, which is effective to reduce erythrocyte dehydration.

In a fifth aspect, the invention provides a method of treating or preventing sickle cell disease. The method comprises administering to a subject suffering sickle cell disease a therapeutically effective amount of a compound having a structure according to Formula I.

In a sixth aspect, the present invention provides a method for reducing intraocular pressure. The method includes delivering to an eye, an amount of a compound according to Formula I sufficient to lower said intraocular pressure.

In a seventh aspect, the invention provides a method of treating or preventing glaucoma. The method comprises delivering to a subject suffering from or at risk of developing glaucoma a therapeutically effective amount of a compound according to Formula I.

In another aspect, the invention is also directed to methods of treating or preventing mammalian cell proliferation. Thus, in another aspect, the invention provides methods of inhibiting mammalian cell proliferation as an approach towards the treatment or prevention of diseases characterized by unwanted or abnormal cell proliferation. In its broadest sense, these methods involve only a single step-the administration of an effective amount of at least one pharmacologically active compound according to the invention to a mammalian cell in situ. In exemplary embodiment, the compounds may act cytostatically, cytotoxically, or by a combination of both mechanisms to inhibit cell proliferation. Mammalian cells treatable in this manner include, e.g., vascular smooth muscle cells, fibroblasts, endothelial cells, various pre-cancer cells and various cancer cells. In a preferred embodiment, cell proliferation is inhibited in a subject suffering from a disorder that is characterized by unwanted or abnormal cell proliferation. Such diseases are described more fully below.

In an exemplary method of the invention, an effective amount of at least one compound according to the invention, or a pharmaceutical composition thereof, is administered to a patient suffering from a disorder that is characterized by abnormal cell proliferation. While not intending to be bound by any particular theory, it is believed that administration of an appropriate amount of a compound according to the invention to a subject inhibits cell proliferation by altering the ionic fluxes associated with early mitogenic signals. Such alteration of ionic fluxes is thought to be due to the ability of the compounds of the invention to inhibit potassium channels of cells. The method can be used prophylactically to prevent unwanted or abnormal cell proliferation, or may be used therapeutically to reduce or arrest proliferation of abnormally proliferating cells. The compound, or a pharmaceutical formulation thereof, can be applied locally to proliferating cells to arrest or inhibit proliferation at a desired time, or may be administered to a subject systemically to arrest or inhibit cell proliferation.

Diseases which are characterized by abnormal cell proliferation that can be treated or prevented by means of the present invention include, but are not limited to, blood vessel proliferative disorders, fibrotic disorders, atherosclerotic disorders and various cancers. Blood vessel proliferation disorders generally refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferative disorders include arthritis, where new capillary blood vessels invade the joint and destroy cartilage and ocular diseases such as diabetic retinopathy, where new capillaries in the retina invade the vitreous, bleed and cause blindness and neovascular glaucoma.

Another example of abnormal neovascularization is that associated with solid tumors. It is now established that unrestricted growth of tumors is dependent upon angiogenesis and that induction of angiogenesis by liberation of angiogenic factors can be an important step in carcinogenesis. For example, basic fibroblast growth factor (bFGF) is liberated by several cancer cells and plays a crucial role in cancer angiogenesis. The demonstration that certain animal tumors regress when angiogenesis is inhibited has provided the most compelling evidence for the role of angiogenesis in tumor growth. Other cancers that are associated with neovascularization include hemangioendotheliomas, hemangiomas and Kaposi's sarcoma.

Proliferation of endothelial and vascular smooth muscle cells is the main feature of neovascularization. The invention is useful in inhibiting such proliferation, and therefore in inhibiting or arresting altogether the progression of the angiogenic condition which depends in whole or in part upon such neovascularization. The invention is particularly useful when the condition has an additional element of endothelial or vascular smooth muscle cell proliferation that is not necessarily associated with neovascularization. For example, psoriasis may additionally involve endothelial cell proliferation that is independent of the endothelial cell proliferation associated with neovascularization. Likewise, a solid tumor which requires neovascularization for continued growth may also be a tumor of endothelial or vascular smooth muscle cells. In this case, growth of the tumor cells themselves, as well as the neovascularization, is inhibited by the compounds described herein.

The invention is also useful for the treatment of fibrotic disorders such as fibrosis and other medical complications of fibrosis which result in whole or in part from the proliferation of fibroblasts. Medical conditions involving fibrosis (other than atherosclerosis, discussed below) include undesirable tissue adhesion resulting from surgery or injury.

Other cell proliferative disorders which can be treated by means of the invention include arteriosclerotic conditions. Arteriosclerosis is a term used to describe a thickening and hardening of the arterial wall. An arteriosclerotic condition as used herein means classical atherosclerosis, accelerated atherosclerosis, atherosclerotic lesions and any other arteriosclerotic conditions characterized by undesirable endothelial and/or vascular smooth muscle cell proliferation, including vascular complications of diabetes.

Proliferation of vascular smooth muscle cells is a main pathological feature in classical atherosclerosis. It is believed that liberation of growth factors from endothelial cells stimulates the proliferation of subintimal smooth muscle which, in turn, reduces the caliber and finally obstructs the artery. The invention is useful in inhibiting such proliferation, and therefore in delaying the onset of, inhibiting the progression of, or even halting the progression of such proliferation and the associated atherosclerotic condition.

Proliferation of vascular smooth muscle cells produces accelerated atherosclerosis, which is the main reason for failure of heart transplants that are not rejected. This proliferation is also believed to be mediated by growth factors, and can ultimately result in obstruction of the coronary arteries. The invention is useful in inhibiting such obstruction and reducing the risk of, or even preventing, such failures.

Vascular injury can also result in endothelial and vascular smooth muscle cell proliferation. The injury can be caused by any number of traumatic events or interventions, including vascular surgery and balloon angioplasty. Restenosis is the main complication of successful balloon angioplasty of the coronary arteries. It is believed to be caused by the release of growth factors as a result of mechanical injury to the endothelial cells lining the coronary arteries. Thus, by inhibiting unwanted endothelial and smooth muscle cell proliferation, the compounds described herein can be used to delay, or even avoid, the onset of restenosis.

Other atherosclerotic conditions which can be treated or prevented by means of the present invention include diseases of the arterial walls that involve proliferation of endothelial and/or vascular smooth muscle cells, such as complications of diabetes, diabetic glomerulosclerosis and diabetic retinopathy.

The compounds described herein are also useful in treating or preventing various types of cancers. Cancers which can be treated by means of the present invention include, but are not limited to, biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute and chronic lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor.

The compounds of the invention are useful with hormone dependent and also with nonhormone dependent cancers. They also are useful with prostate and nonprostate cancers and with breast and nonbreast cancers. They further are useful with multidrug resistant strains of cancer.

In addition to the particular disorders enumerated above, the invention is also useful in treating or preventing dermatological diseases including keloids, psoriasis, dermatitis, hypertrophic scars, seborrheic dermatosis, papilloma virus infection (e.g., producing verruca vulgaris, verruca plantaris, verruca plan, condylomata, etc.), eczema and epithelial precancerous lesions such as actinic keratosis. Other inflammatory disease states may also benefit from the methods described herein including arthritis, chronic obstructive pulmonary disease (COPD), acute respiratory distress syndrome (ARDS), asthma and other respiratory ailments mediated by the inflammatory process; atherosclerosis; keratoconjunctivitis; uveitis; inflammatory bowel disease; proliferative glomerulonephritis; lupus erythematosus (and other auto-immune diseases); scleroderma; temporal arthritis; thromboangiitis obliterans; mucocutaneous lymph node syndrome; and other pathologies mediated by growth factors including uterine leiomyomas; multiple sclerosis; shock, sepsis; ischemia; and reperfusion injury.

These and other objects and advantages of the present invention will be apparent from the detailed description and examples that follow. All publications, patents and patent applications are incorporated herein by reference in their entirety.

DETAILED DESCRIPTION OF THE INVENTION AND THE PREFERRED EMBODIMENTS

Abbreviations and Definitions

Figure 1A:
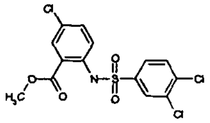
FIGURE 1 displays structures of representative compounds of the invention.

The abbreviations used herein have their conventional meaning within the chemical and biological arts. For example: $Et_3N$, triethylamine; MeOH, methanol; and DMSO, dimethylsulfoxide; MCHC, mean corpuscular hemoglobin concentration; SAD-1, a transgenic mouse model of sickle cell disease as described by Trudel et. al., *EMBO J.,* 10 (11): 3157–3165 (1991).

"Blocking" and "inhibiting," are used interchangeably herein to refer to the partial or full blockade of an intermediate conductance, calcium activated potassium channel by one or more compound(s) of the invention.

Where substituent groups are specified by their conventional chemical formulae, written from left to right, they equally encompass the chemically identical substituents which would result from writing the structure from right to left, e.g., $—CH_2O—$ is intended to also recite $—OCH_2—$.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by $—CH_2CH_2CH_2CH_2—$, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH{=}CH—N(CH_3)—CH_3$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$–$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term “aryl” when used in combination with other terms (e.g., aryloxy, arylthioxy, arylalkyl) includes both aryl and heteroaryl rings as defined above. Thus, the term “arylalkyl” is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., “alkyl,” “heteroalkyl,” “aryl” and “heteroaryl”) are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R'', —SR', —halogen, —SiR'R''R''', —OC(O)R', —C(O)R', $—CO_2R'$, —CONR'R'', —OC(O)NR'R'', —NR''C(O)R', —NR'—C(O)NR''R''', $—NR''C(O)_2R'$, —NR—C(NR'R''R''')=NR'''', —NR—C(NR'R'')=NR''', —S(O)R', $—S(O)_2R'$, $—S(O)_2NR'R''$, $—NRSO_2R'$, —CN and $—NO_2$ in a number ranging from zero to (2m'+1), where m' is the total number of carbon atoms in such radical. R', R'', R''' and R'''' each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: halogen, —OR', =O, =NR', =N—OR', —NR'R'', —SR', -halogen, —SiR'R''R''', —OC(O)R', —C(O)R', $—CO_2R'$, —CONR'R'', —OC(O)NR'R'', —NR''C(O)R', —NR'—C(O)NR''R''', $—NR''C(O)_2R'$, —NR—C(NR'R''R''')=NR'''', —NR—C(NR'R'')=NR''', —S(O)R', $—S(O)_2R'$, $—S(O)_2NR'R''$, $—NRSO_2R'$, —CN and $—NO_2$, —R', $—N_3$, $—CH(Ph)_2$, fluoro($C_1$–$C_4$)alkoxy, and fluoro($C_1$–$C_4$)alkyl, in a number ranging from zero to the total number of open valences on the aromatic ring system; and where R', R'', R''' and R'''' are preferably independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally be replaced with a substituent of the formula—T—C(O)—$(CRR')_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula—A—$(CH_2)_r$—B—, wherein A and B are independently —CRR'—, —O—, —NR—, —S—, —S(O)—, $—S(O)_2—$, $—S(O)_2NR'—$ or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X—$(CR''R''')_d$—, where s and d are independently integers of from 0 to 3, and X is —O—, —NR'—, —S—, —S(O)—, $—S(O)_2—$, or $—S(O)_2NR'—$. The substituents R, R', R'' and R''' are preferably independently selected from hydrogen or substituted or unsubstituted ($C_1$–$C_6$)alkyl.

As used herein, the term “heteroatom” is meant to include oxygen (O), nitrogen (N), sulfur (S) and silicon (Si).

The term “pharmaceutically acceptable salts” is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., “Pharmaceutical Salts”, *Journal of Pharmaceutical Science,* 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are intended to be encompassed within the scope of the present invention.

The term "glaucoma" refers to an optic neuropathy or degenerative state usually associated with elevation of intraocular pressure. See, Shields, TEXTBOOK OF GLAUCOMA ($4^{th}$ Ed.), 1997, Lippincott, Williams and Wilkins, which is incorporated herein by reference. The mechanism by which elevated eye pressure injures the optic nerve is not well understood. It is known that axons entering the inferotemporal and superotemporal aspects of the optic disc are damaged. As fibers of the disc are destroyed, the neural rim of the optic disc shrinks and the physiologic cup within the optic disc enlarges. A term known as pathologic "cupping" refers to this shrinking and enlarging process. Although it is possible to measure the cup-to-disc ratio, it is not a useful diagnostic tool because it varies widely in the population. However, it can be used to measure the progression of the disease by a series of measurements in a time period.

Glaucoma is not a single disease but a group of conditions with various causes. In most cases, these conditions produce increased pressure within the eye. Ultimately glaucoma can lead to optic nerve damage and the loss of visual function. It is not unusual for persons who exhibit gradual development of intraocular pressure to exhibit no symptoms until the end-stage of the disease is reached.

The term "open angle glaucoma"—refers to a chronic type of glaucoma. Occurring in approximately 1% of Americans, open-angle glaucoma is the most common type of glaucoma. Open-angle glaucoma is characterized by a very gradual, painless rise of pressure within the eye. Subjects with open-angle glaucoma exhibit no outward manifestations of disease until irreversible vision impairment.

"Normal tension glaucoma" commonly referred to as low tension glaucoma is a form of open angle glaucoma that accounts for about ⅓ of open-angle glaucoma cases in the United States.

"Angle closure glaucoma" is a glaucoma most prevalent in people who are far-sighted. In angle closure glaucoma, the anterior chamber of the eye is smaller than average hampering the ability of the aqueous humor to pass between the iris and the lens on its way to the anterior chamber, causing fluid pressure to build up between the iris.

"Acute glaucoma" is caused by a sudden increase in intraocular pressure. This intense rise in pressure is accompanied by severe pain. In acute glaucoma, there are outward manifestations of the disease including red eye, cornea swelling and clouding over.

The term "pigmentary glaucoma" refers to a hereditary condition which develops more frequently in men than in woman and begins in the twenties or thirties pigmentary glaucoma affects persons of near-sightedness. Myopic eyes have a concave-shaped iris creating an unusually wide angle. The wideness of the angle causes the pigment layer of the eye to rub on the lens when the pupil constricts and dilates during normal focusing. The rubbing action ruptures the cells of the iris pigment epithelium, thereby releasing pigment particles into the aqueous humor and trabecular meshwork. If pigment plugs the pores of the trabecular meshwork, drainage is inhibited.

The term "exfoliation syndrome" refers to a type of glaucoma most common in persons of European descent. Exfoliation syndrome is characterized by a whitish material that builds on the lens of the eye. Movement of the iris causes this material to be rubbed off the lens along with some pigment from the iris. Both the pigment and the whitish exfoliation material clog the meshwork, inhibiting drainage of the aqueous humor.

The term "trauma related Glaucoma" refers to a type of glaucoma caused by an external force acting upon the eye, i.e., chemical burn, blow to the eye. Trauma related glaucoma occurs when this external force causes a mechanical disruption or physical change with in the eye's drainage system.

"Congenital glaucoma" occurs in about 1 in 10,000 births. It may appear up until age 4. Primary congenital glaucoma is due to abnormal development of the trabecular meshwork. Congenital glaucoma can be hereditary as well as non-hereditary. In congenital glaucoma, the eye enlarges or the cornea becomes hazy. The stretching of the cornea causes breaks to occur in the inner lining. The breaks allow aqueous humor to enter the cornea causing it to swell. As the cornea continues to stretch, more aqueous humor is let in and there is an increase in edema and haze in the cornea.

The term "Sturge-Weber Syndrome" refers to a rare syndrome characterized by a facial birthmark port wine in color. The birthmark is associated with an abnormal blood vessels on the surface of the brain. These vascular malformations may affect the eyelids, sclera, conjunctiva, and iris. One third of patients with Sturge-Weber syndrome suffer from increased intraocular pressure. This increased pressure leads to glaucoma. A vascular malformation of the sclera causes elevated pressure in the veins. This elevated pressure in the veins drains the eye thereby causing the intraocular pressure to rise and resulting in damage to the drainage system of the eye.

The term "uveitis" refers to a disease characterized by inflammation of the choroid, ciliary body and iris. In anterior uveitis, a decrease in aqueous humor formation may cause dangerously low levels of pressure within the eye. In other forms of uveitis, i.e., posterior uveitis, the intraocular pressure is elevated. The elevation may be caused by active inflammation, insufficient anti-inflammatory therapy, excessive corticosteroid use or insufficient glaucoma therapy. If the inflammation is chronic and not properly controlled, it can lead to trabecular cell death.

The term "chronic elevation" refers to increased pressure caused by a condition that is reoccurring and not treatable.

The term “acute elevation” refers to a sudden increase in intraocular eye pressure. The sudden rise can occur within hours and causes pain within the eye and may even cause nausea and vomiting The term “gradual elevation” refers to a slow increase of pressure within the eye. There are no symptoms associated with the increased rise.

An “ophthalmically acceptable carrier” is a carrier that has substantially no long term or permanent detrimental effect on the eye to which it is administered.

Introduction

As discussed above, the blockade of the intermediate conductance, calcium activated potassium channel is a powerful therapeutic approach for the treatment of disease states in which said channel plays a therapeutically relevant role as a drug target. Representative diseases that may be treated by inhibition of the intermediate conductance, calcium activated potassium channel include, but are not limited to sickle cell disease, inflammation and glaucoma.

The present invention is illustrated by reference to the use of the compounds of the invention in treating sickle cell disease and glaucoma. The focus on the two selected diseases is for clarity of illustration only and is not intended to define or otherwise limit the scope of the present invention.

The prevention of sickle cell dehydration via inhibition of the intermediate conductance, calcium activated potassium channel (i.e., the Gardos channel) is useful in the treatment and/or prevention of sickle cell disease. Moreover, physiological studies show that intermediate conductance, calcium activated potassium channels play a role in secretion of $Cl^-$ and water from epithelial tissue. Given that the intraocular pressure of the eye is maintained, in part, by secretion of aqueous humor, the inhibition of aqueous humor secretion by an antagonist of the intermediate conductance, calcium activated potassium channel reduces intraocular pressure. For example, in rabbits, topical application of a compound of the invention was demonstrated to result in a dose-dependent, long duration reduction in intraocular pressure. Thus, the blockade of intermediate conductance, calcium activated potassium channels in the eye is of benefit for the treatment of glaucoma.

The present invention provides sulfonamide compounds, compositions containing these compounds, and methods for using these compounds and compositions to decrease ion flux in intermediate conductance, calcium activated potassium channels. Inhibition of said channel reduces mammalian cell proliferation, intraocular pressure, erythrocyte dehydration, sickle cell dehydration, and delays the occurrence of acute sickle cell episodes. Thus, the present invention also provides methods of using the compounds of the invention to treat and prevent diseases in which inhibition of ion flux through intermediate conductance, calcium activated potassium channels may prove beneficial.

DESCRIPTION OF THE EMBODIMENTS

I. Modulators of Intermediate Conductance Calcium Activated Potassium Channels

In a first aspect, the present invention provides compounds according to Formula I:

(I)

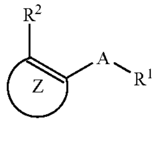

in which the ring system Z is selected from substituted or unsubstituted aryl, substituted or unsubstituted carbocycle, substituted or unsubstituted heteroaryl, or substituted or unsubstituted heterocycloalkyl. The symbol A represents $-NHS(O)_2-$, $-S(O)_2NH-$, $-C(R^4R^5)S(O)_n-$, $-S(O)_nC(R^4R^5)-$, $-C(R^4R^5)NHS(O)_n-$, $-S(O)_nNHC(R^4R^5)-$, $-C(R^4R^5)S(O)_nNH-$, or $-HNS(O)_nC(R^4R^5)-$. The symbol $R^1$ represents a substituted or unsubstituted aryl group, a substituted or unsubstituted heteroaryl group, a substituted or unsubstituted carbocycle, or substituted or unsubstituted heterocycloalkyl. The symbol $R^2$ represents $COOR^3$, substituted or unsubstituted 2-furan, substituted or unsubstituted 2-thiazole or

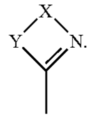

The symbol $R^3$ represents a substituted or unsubstituted $C_1$-$C_4$ alkyl group, e.g, methyl, ethyl, or $-CF_3$. X represents $-N{=}N-$, $-N{=}C(R^4)-$, $-C(R^4){=}N-$, $-C(R^4R^5)-C(R^4R^5)-$ or $-C(R^4){=}C(R^5)-$, in which $R^4$ and $R^5$ independently represent hydrogen, halogen, substituted and unsubstituted lower alkyl, $-OR^6$ or $-CF_3$. The symbol Y represents O, $NR^{11}$ or S, in which $R^{11}$ is $-H$, lower alkyl or $-CF_3$. The symbol $R^6$ represents a member selected from hydrogen, or substituted or unsubstituted lower alkyl.

In an exemplary embodiment, the invention provides compounds as described above in which Z is selected from substituted or unsubstituted phenyl and substituted or unsubstituted thiophene. In another exemplary embodiment, compounds of the invention include a group for $R^2$ that is selected from substituted or unsubstituted 2-furan, and

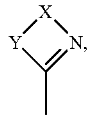

in which X is $-N{=}C(R^4)-$, $-C(R^4){=}N-$, $-C(R^4R^5)-C(R^4R^5)-$ or $-C(R^4){=}C(R^5)-$; and Y is O or S.

In yet another exemplary embodiment, $R^1$ is a selected from

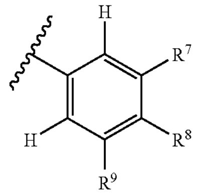

and

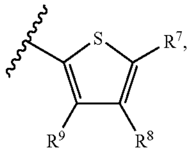

in which the symbols $R^7$, $R^8$ and $R^9$ independently represent H, halogen, lower alkyl, $OR^{10}$, $-OCF_3$, $CF_3$, and $NO_2$. The symbol $R^{10}$ represents H, lower alkyl, or substituted lower alkyl.

In a still further exemplary embodiment, the invention provides compounds in which the symbol $R^1$ represents the group:

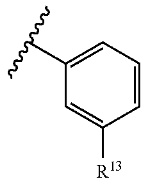

wherein $R^{13}$ is a member selected from halogen, substituted or unsubstituted $C_1$–$C_4$ alkyl, $CF_3$ and $OCF_3$.

Figure 1A:
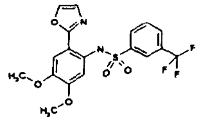
Figure 1A:
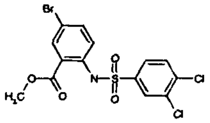
Figure 1A:
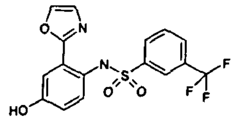
Figure 1A:
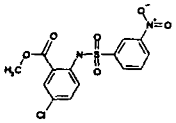
Figure 1A:
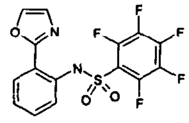
Figure 1A:
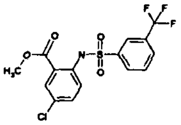
Figure 1A:
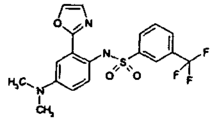
Figure 1A:
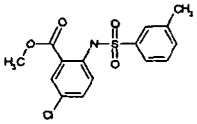
Figure 1A:
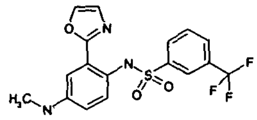
Figure 1A:
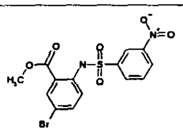
Figure 1A:
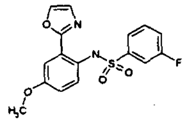
Figure 1A:
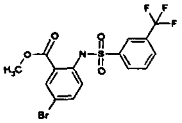
Figure 1A:
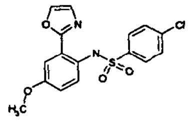
Figure 1A:
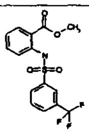
Figure 1A:
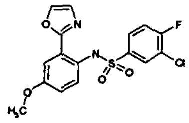
Figure 1A:
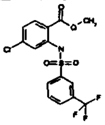
Figure 1A:
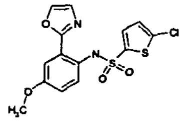
Figure 1A:
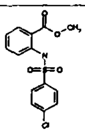
Figure 1A:
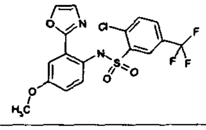
Figure 1A:
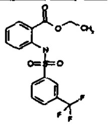
Figure 1A:
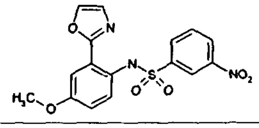
Figure 1A:
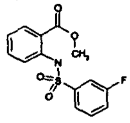
Figure 1A:
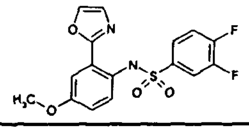
Figure 1B:
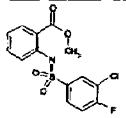
Figure 1B:
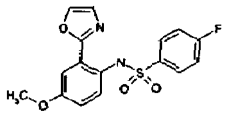
Figure 1B:
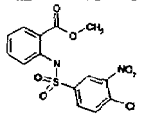
Figure 1B:
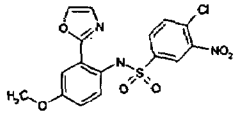
Figure 1B:
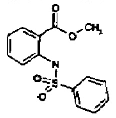
Figure 1B:
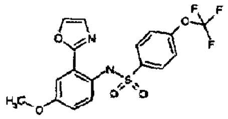
Figure 1B:
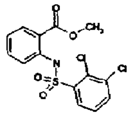
Figure 1B:
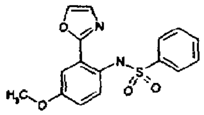
Figure 1B:
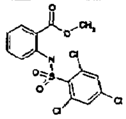
Figure 1B:
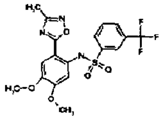
Figure 1B:
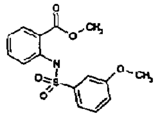
Figure 1B:
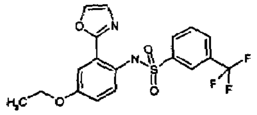
Figure 1B:
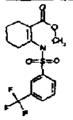
Figure 1B:
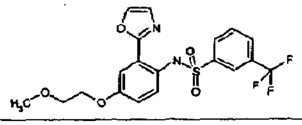
Figure 1B:
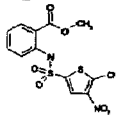
Figure 1B:
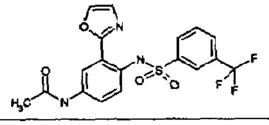
Figure 1B:
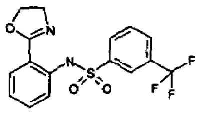
Figure 1B:
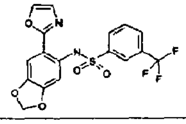
Figure 1B:
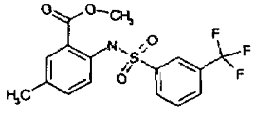
Figure 1B:
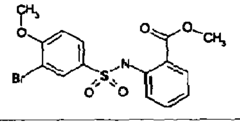
Figure 1B:
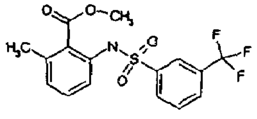
Figure 1B:
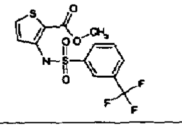
Figure 1B:
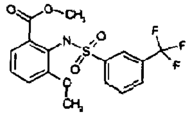
Figure 1B:
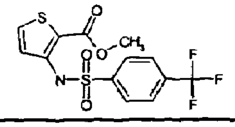
Figure 1C:
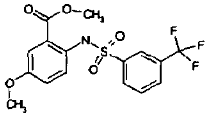
Figure 1C:
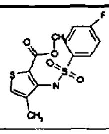
Figure 1C:
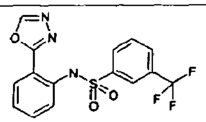
Figure 1C:
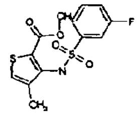
Figure 1C:
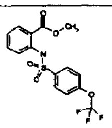
Figure 1C:
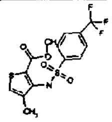
Figure 1C:
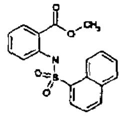
Figure 1C:
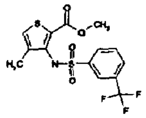
Figure 1C:
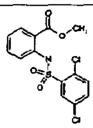
Figure 1C:
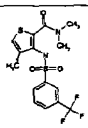
Figure 1C:
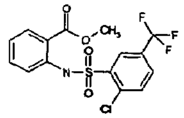
Figure 1C:
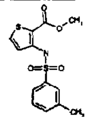
Figure 1C:
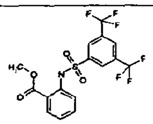
Figure 1C:
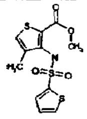
Figure 1C:
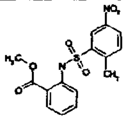
Figure 1C:
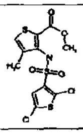
Figure 1C:
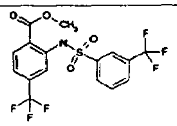
Figure 1C:
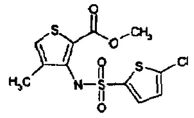
Figure 1C:
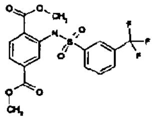
Figure 1C:
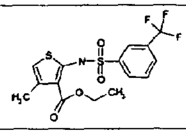
Figure 1C:
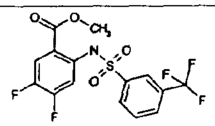
Figure 1C:
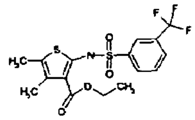
Figure 1C:
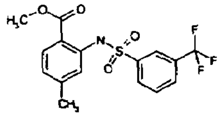
Figure 1C:
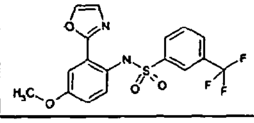
Figure 1D:
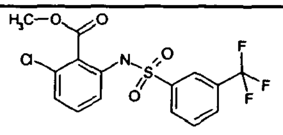
Figure 1D:
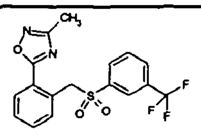
Figure 1D:
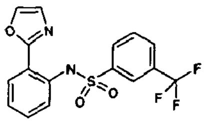
Figure 1D:
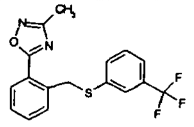
Figure 1D:
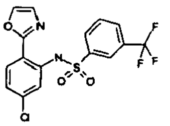
Figure 1D:
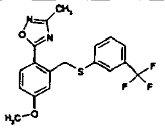
Figure 1D:
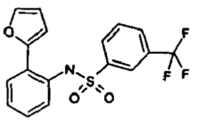
Figure 1D:
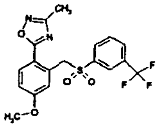
Figure 1D:
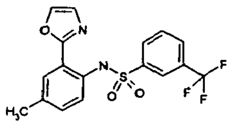
Figure 1D:
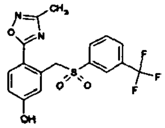
Figure 1D:
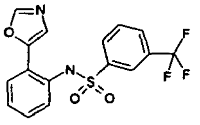
Figure 1D:
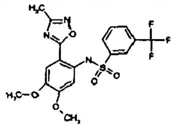
Figure 1D:
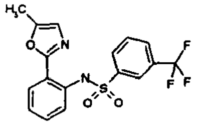
Figure 1D:
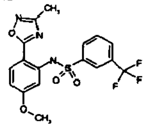
Figure 1D:
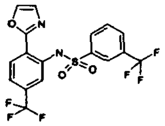
Figure 1D:
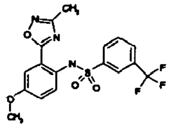
Figure 1D:
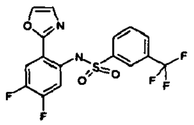
Figure 1D:
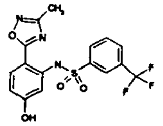
Figure 1D:
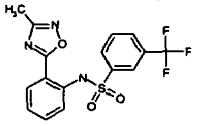
Figure 1D:
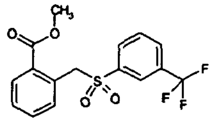
Figure 1D:
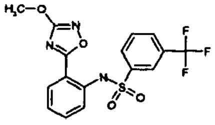
Figure 1D:
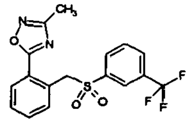
Figure 1D:
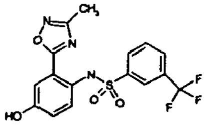
Figure 1D:
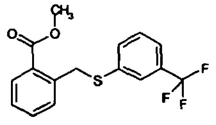
Figure 1E:
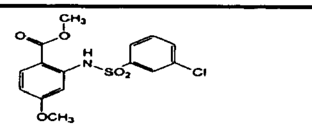
Figure 1E:
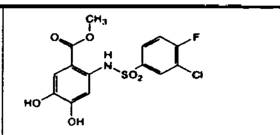
Figure 1E:
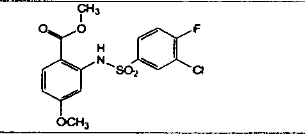
Figure 1E:
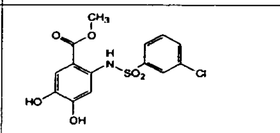
Figure 1E:
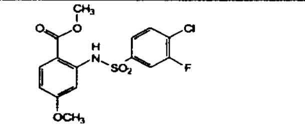
Figure 1E:
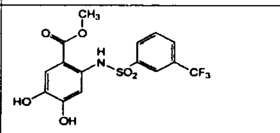
Figure 1E:
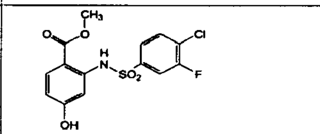
Figure 1E:
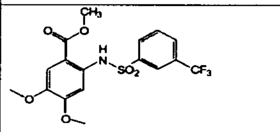
Figure 1E:
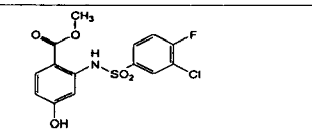
Figure 1E:
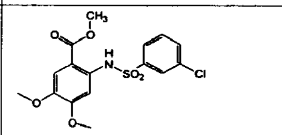
Figure 1E:
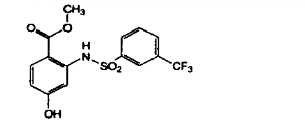
Figure 1E:
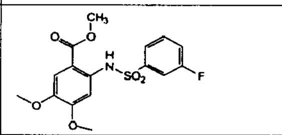
Figure 1E:
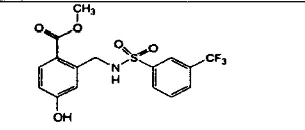
Figure 1E:
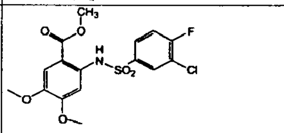
Figure 1E:
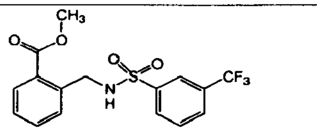
Figure 1E:
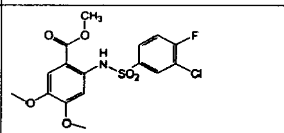
Figure 1E:
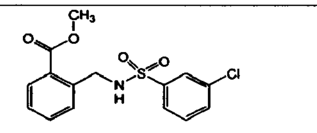
Figure 1E:
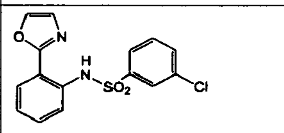
Figure 1E:
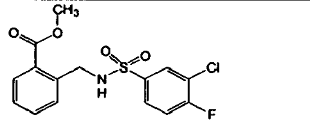
Figure 1E:
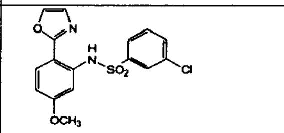
Figure 1E:
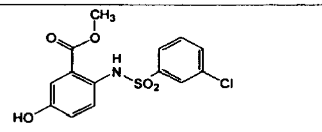
Figure 1E:
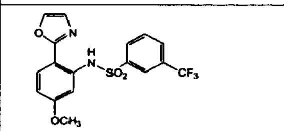
Figure 1E:
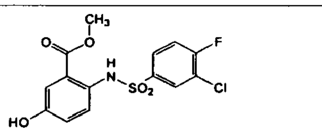
Figure 1E:
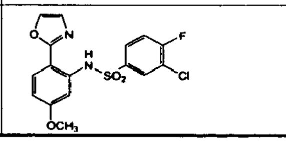
Figure 1F:
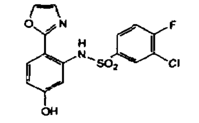
Figure 1F:
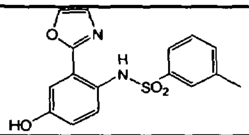
Figure 1F:
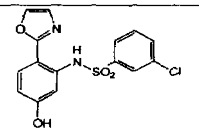
Figure 1F:
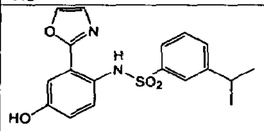
Figure 1F:
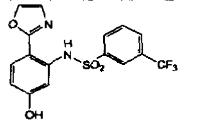
Figure 1F:
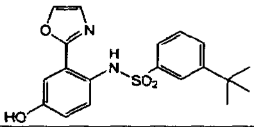
Figure 1F:
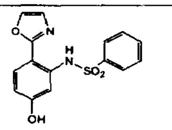
Figure 1F:
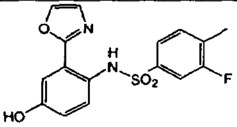
Figure 1F:
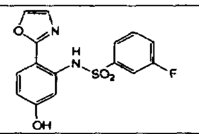
Figure 1F:
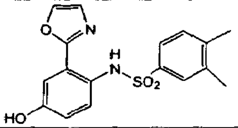
Figure 1F:
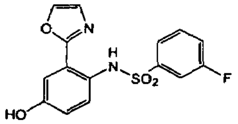
Figure 1F:
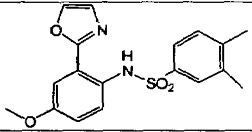
Figure 1F:
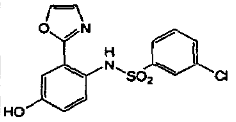
Figure 1F:
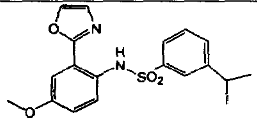
Figure 1F:
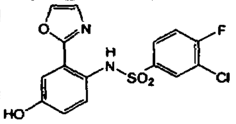
Figure 1F:
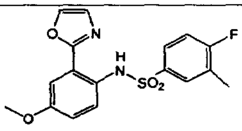
Figure 1F:
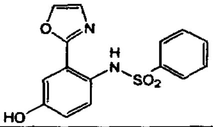
Figure 1F:
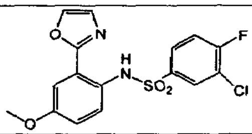
Figure 1F:
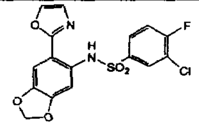
Figure 1F:
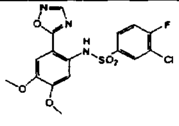
Figure 1F:
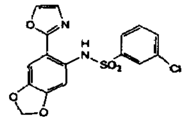
Figure 1F:
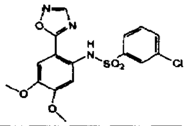
Figure 1F:
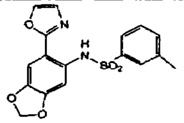
Figure 1F:
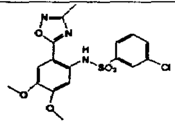
Figure 1G:
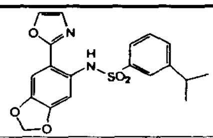
Figure 1G:
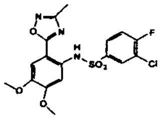
Figure 1G:
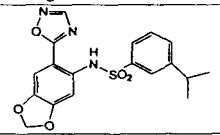
Figure 1G:
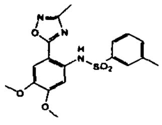
Figure 1G:
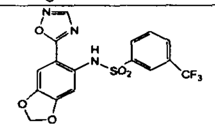
Figure 1G:
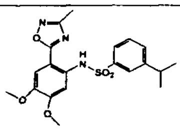
Figure 1G:
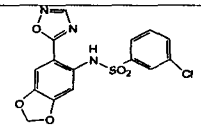
Figure 1G:
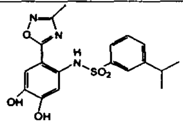
Figure 1G:
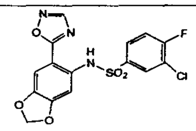
Figure 1G:
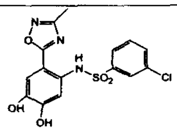
Figure 1G:
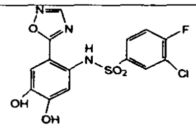
Figure 1G:
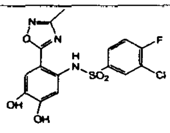
Figure 1G:
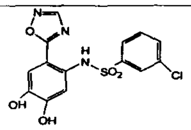
Figure 1G:
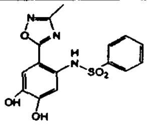
Figure 1G:
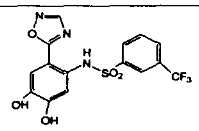
Figure 1G:
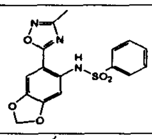
Figure 1G:
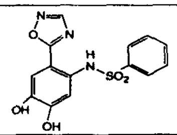
Figure 1G:
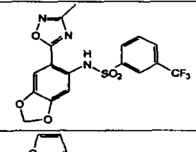
Figure 1G:
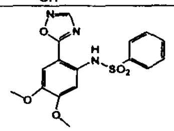
Figure 1G:
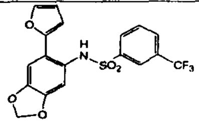
Figure 1G:
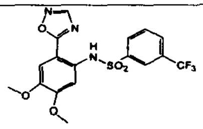
Figure 1G:
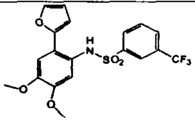
Figure 1G:
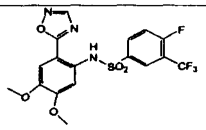
Figure 1G:
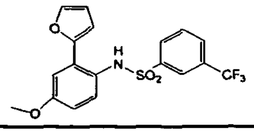
Figure 1H:
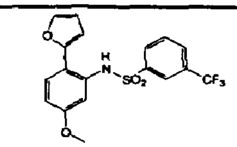
Figure 1H:
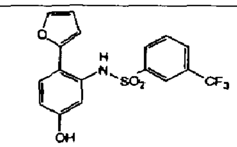
Figure 1H:
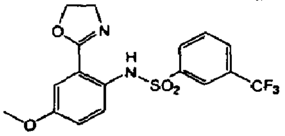
Figure 1H:
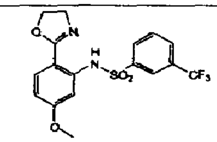
Figure 1H:
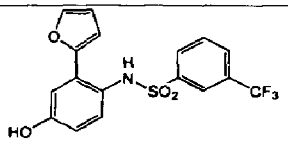
Figure 1H:
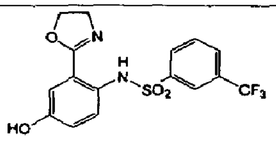
Figure 1H:
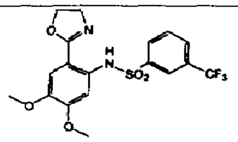

Representative compounds of the invention according to Formula I are set forth in FIG. 1.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having a water-solubility that is enhanced relative to analogous compounds that are not similarly functionalized. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Potassium Channel Blockers

Compounds of the present invention can be prepared using readily available starting materials or known intermediates. For example, furan derivatized bis-aryl sulfonamides are readily prepared the method of Scheme A:

Scheme A

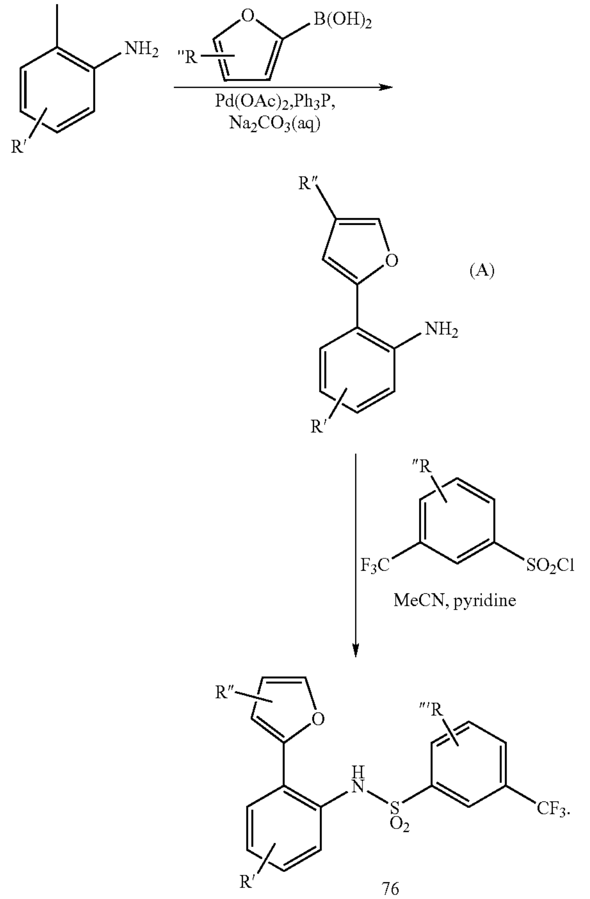

76

Scheme A

In Scheme A, and each of the succeeding schemes, each of the reaction components can bear one or more substituents ("R groups") other than a locus of reaction. The symbols R', R", R'", etc. generally represent substituents for aryl or heteroaryl groups as described in the definitions section herein.

In scheme A, the iodo aniline substrate a is coupled with the furan moiety via a Pd mediated reaction with a boronic acid derivative to afford compound b. The resulting adduct is reacted with an activated sulfonic acid derivative to produce adduct c.

Scheme B

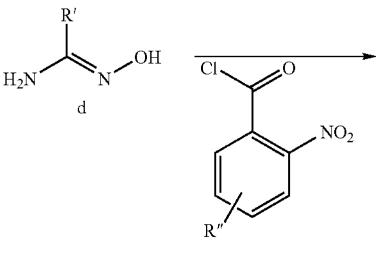

d

-continued

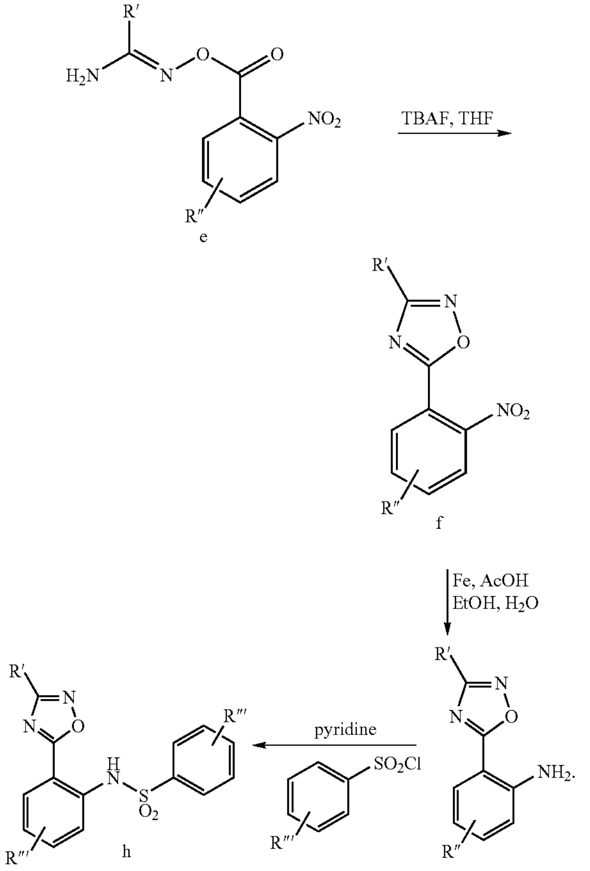

e f g h

Scheme B

Scheme B sets out an exemplary route to oxadiazolyl-containing compounds of the invention. Thus, amidine d is acylated with a benzoyl chloride species, affording compound e. Compound e is cyclized to compound f. The nitro group of compound f is reduced and the resulting amine is converted to the correspond sulfonamide h.

Scheme C

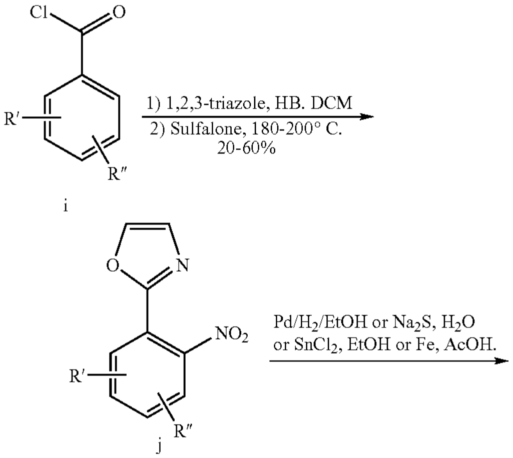

i j

-continued

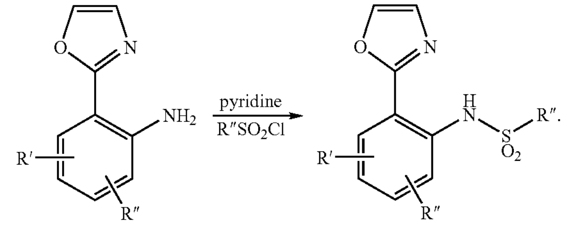

k l

Scheme C

Scheme C sets forth a representative route to oxazole-containing compounds of the invention. Acyl halide i is converted to oxazole j by the action of triazole in sulfalone. The nitro group of j is reduced, affording the corresponding amine k, which is converted to a sulfone l by the action of an activated sulfonic acid derivative.

Scheme D

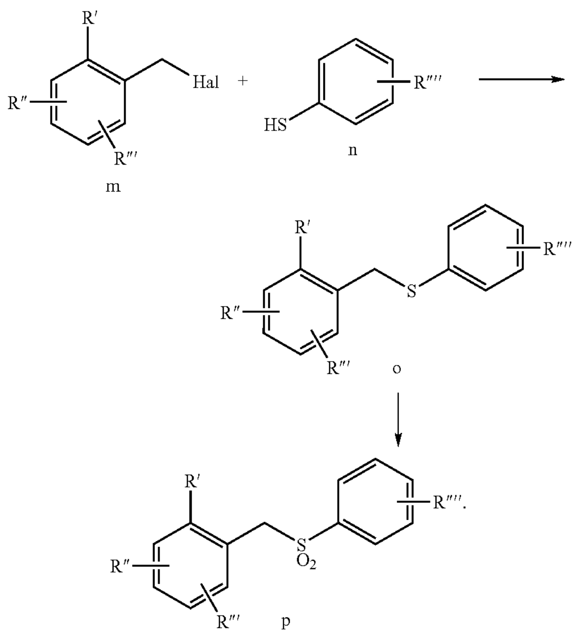

m n o p

Scheme D

Scheme D provides an exemplary route to bis-aryl sulfonamides of the invention. Benzyl halide m is reacted with an appropriate thiol n, forming sulfide o, which is subsequently oxidized to sulfonamide p.

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a hetereofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

Compound Stability

Compounds of the present invention useful as intermediate conductance, calcium activated potassium channel inhibitors, preferably exhibit both acceptable bioavailability and stability in vivo. The stability of the compounds of the invention in various biological milieus can be assayed by methods known in the art. In one embodiment, the stability of the compounds is assayed in an in vitro preparation. In a preferred embodiment, the in vitro preparation is a liver microsome preparation. The results of such in vitro assays provide data relevant to the in vivo stability of the compounds of the invention. Other in vitro assays useful in assaying the stability of the compounds of the invention are known in the art.

In addition to in vitro methods, in vivo methods such as pharmacokinetic studies can be performed in a range of animal models. One or more compounds of the invention can be administered to an animal, preferably a rat, at different dosages and/or by different routes (e.g., i.v., i.p., p.o). Blood, urine and/or feces samples can be collected at serial time points and the samples assayed for the presence and/or concentration of the compound(s) of the invention and/or the metabolites of the compound(s).

Any appropriate quantity can be utilized to compare data from different compounds. Exemplary quantities include, half-life, bioavailability, amount of compound remaining intact after a predetermined time period and the like. In a preferred embodiment, the amount of compound remaining intact after a predetermined time period is utilized. As used herein, "intact" refers to compound that has not been metabolized or other wise degraded into a species different from the original compound.

Any technique that allows the detection and, preferably, the quantitation of the compound(s) and/or metabolites is appropriate for use in assaying the compounds of the invention. These methods include, but are not limited to, spectrometric methods (e.g., NMR (e.g., $^{19}$F NMR), MS, IR, UV/vis), chromatographic methods (e.g., LC, GC, HPLC) and hybrid methods utilizing both spectrometric and chromatographic methods (e.g., GC/MS, LC/MS, LC/MS/MS). Further, the methods can utilize detectable labels such as compounds of the invention that are labeled with radioisotopes (e.g., $^{3}$H, $^{15}$N, $^{14}$C) or fluorescent labels (e.g., fluorescein, rhodamine). Other methods for assaying the in vivo persistence of small organic molecules, particularly those applicable to bioactive molecules, will be apparent to those of skill in the art.

Compound Activity

To develop pharmaceutically useful intermediate conductance, calcium activated potassium channel inhibitors, candidate compounds must demonstrate acceptable activity towards the target channel. The activity of the compounds of the invention towards these ion channels, such as the Gardos channel, can be assayed utilizing methods known in the art.

Compounds that decrease ion flow through intermediate conductance, calcium activated potassium channels are tested using biologically active channels, either recombinant or naturally occurring. Intermediate conductance, calcium activated potassium channels, preferably human channels, can be found in native cells, isolated in vitro, co-expressed or expressed in a cell, or expressed in membrane derived from a cell. Modulation by a compound of the invention is tested using standard in vitro or in vivo assays such as those well known in the art or as otherwise described herein. Compounds that decrease the flux of ions will cause a detectable decrease in the ion current density by decreasing the probability of the channel being open, by increasing the probability of it being closed, by decreasing conductance through the channel, and by hampering the passage of ions.

Decreased flux of potassium may be assessed by determining changes in polarization (i.e., electrical potential) of a cell which expresses, for example, the intermediate conductance, calcium activated potassium channel known as the Gardos channel. One method of determining changes in cellular polarization is the voltage-clamp technique e.g., the "cell attached" mode, the "inside out" mode, and the "whole cell" mode (see, e.g., Ackerman et al., *New Engl. J. Med.* 336:1575–1595 (1997)). Other known assays include radiolabeled rubidium flux assays and fluorescence assays using voltage-sensitive dyes. See, e.g., Vestergarrd-Bogind et al., *J. Membrane Biol.,* 88:67–75 (1988); Danel et al., *J Pharmacol. Meth.,* 25:185–193 (1991); Holevinsky et al., *J. Membrane Biology,* 137:59–70 (1994). Assays for compounds capable of inhibiting or increasing potassium flux through the intermediate conductance, calcium activated potassium channel protein can be performed by application of the compounds to a bath solution in contact with and comprising cells having said channel. See, e.g., Blatz et al., *Nature,* 323:718–720 (1986); Park, *J. Physiol.,* 481:555–570 (1994). Generally the compounds to be tested are present in the range from 1 pM to 100 mM. Changes in function of the channels can be measured in the electrical currents or ionic flux, or by the consequences of changes in currents and flux.

The effects of the test compounds upon the function of the channels can be measured by changes in the electrical currents or ionic flux or by the consequences of changes in currents and flux. Changes in electrical current or ion flux are measured either by increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological parameter can be used to assess the influence of a test compound on the channels of this invention. Changes in channel function can be measured by ligand displacement such as CTX release. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immune-responses (e.g., T cell activation), changes in cell metabolism such as cell growth or pH changes.

For compounds of interest in the modulation of sickle cell disease, the inhibition by test compounds of an erythrocyte Gardos channel can be assayed using human red blood cells. The degree of inhibition can be measured using a detectable material such as $^{86}$Rb. In an exemplary assay, utilizing $^{86}$Rb, Gardos channel inhibition can be assayed by exposing red blood cells to $^{86}$Rb and a test compound and measuring the amount of $^{86}$Rb taken up by the cells. Numerous variations on this assay will be apparent to those of skill in the art.

The potency of the compounds of the invention can be assayed using erythrocytes by a method such as that disclosed by Brugnara et al., *J. Clin. Invest.,* 92: 520–526 (1993); and Brugnara et al., *J. Biol. Chem.,* 268(12): 8760–8768 (1993). Utilizing the methods described in these references, both the percent inhibition of the Gardos channel and the $IC_{50}$ of the compounds of the invention can be assayed. Briefly, erythrocytes are exposed to a test compound and a $^{86}Rb$-containing medium. The initial rate of $^{86}Rb$ transport can be calculated from a parameter such as the linear least square slope of $^{86}Rb$ uptake by the cell(s). Inhibitory constants can be calculated by standard methods using computer-assisted nonlinear curve fitting.

When used to modulate intraocular pressure, the activity of a compound of the invention towards an intermediate conductance, calcium activated potassium channel can be assessed using a variety of in vitro and in vivo assays. In one embodiment, the in vivo assays conducted in mammals and disclosed herein, e.g., the rabbit assay in the examples section, are used to identify intermediate conductance, calcium activated potassium channel blockers for treatment of increased intraocular pressure. In another embodiment, the in vitro assays described herein are used, e.g., radiolabeled rubidium flux. Such assays are used to test for inhibitors of intermediate conductance, calcium activated potassium channels and for the identification of compounds that reduce intraocular pressure in a subject. Assays for modulatory compounds include, e.g., measuring current; measuring membrane potential; measure ion flux; e.g., potassium or rubidium; measuring potassium concentration; measuring second messengers and transcription levels; using potassium-dependent yeast growth assays; measuring intraocular pressure, e.g., by administering a compound able to decrease ion flow through intermediate conductance, calcium activated potassium channels to a subject and measuring changes in intraocular pressure.

Other methods for assaying the activity of ion channels and the activity of agents that affect the ion channels are known in the art. The selection of an appropriate assay methods is well within the capabilities of those of skill in the art who. See, for example, Hille, B., Ionic Channels of Excitable Membranes, Sinaner Associates, Inc. Sunderland, Mass. (1992).

Activities for selected compounds of the invention were determined using the assay set forth in Example 4, and are presented in Table 1.

TABLE 1

Relative potencies, in the intermediate conductance, calcium activated potassium channel blocker assay, for a collection of compounds.

| Compound ID # | Activity |
|---|---|
| 1 | + |
| 4 | ++ |
| 11 | +++ |
| 13 | +++ |
| 16 | ++ |
| 31 | ++ |
| 33 | +++ |
| 40 | +++ |
| 41 | +++ |
| 42 | ++ |
| 48 | + |
| 50 | ++ |
| 74 | ++ |
| 76 | +++ |
| 77 | +++ |
| 82 | ++ |
| 83 | ++ |

TABLE 1-continued

Relative potencies, in the intermediate conductance, calcium activated potassium channel blocker assay, for a collection of compounds.

| Compound ID # | Activity |
|---|---|
| 95 | ++ |
| 96 | + |

+ Represents 10 μM < $IC_{50}$ < 2 μM;
++ represents 2 μM < $IC_{50}$ < 0.5 μM;
+++ represents $IC_{50}$ < 0.5 μM.

II. Pharmaceutical Compositions of Potassium Channel Blockers

In another aspect, the present invention provides pharmaceutical compositions comprising a pharmaceutically acceptable excipient and a compound of the invention.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Any method of administering drugs directly to a mammalian eye may be employed to administer, in accordance with the present invention, the compound or compounds to the eye to be treated. The primary effect on the mammal resulting from the direct administration of the compound or compounds to the mammal's eye is a reduction in intraocular pressure. More preferably, one or more intermediate conductance, calcium activated potassium channel blockers and/or additional compounds known to reduce intraocular pressure are applied topically to the eye or are injected directly into the eye. Particularly useful results are obtained when the compound or compounds are applied topically to the eye in an ophthalmic preparation, e.g., as ocular solutions, suspensions, gels or creams, as examples of topical ophthalmic preparations used for dose delivery.

In accordance with the invention the compounds are typically administered in an ophthalmically acceptable carrier in sufficient concentration so as to deliver an effective amount of the compound or compounds to the eye. The compounds are administered in accordance with the present invention to the eye, typically admixed with an ophthalmically acceptable carrier, and optionally with another compound suitable for treatment of glaucoma and/or reduction of intraocular pressure. Any suitable, e.g., conventional, ophthalmically acceptable carrier may be employed including water (distilled or deionized water), saline and other aqueous media, with or without solubility enhancers such as any of the ophthalmically acceptable beta-cyclodextrins. The compounds may be soluble in the carrier which is employed for their administration, so that the compounds are administered to the eye in the form of a solution. Alternatively, a suspension of the compound or compounds (or salts thereof) in a suitable carrier may also be employed.

When forming compositions for topical administration, the compounds are generally formulated as between about 0.001% to 10% w/v, more preferably between about 0.1% to 5% w/v. In one embodiment, the formulation is 1.0% w/v. In one embodiment, the formulations are solutions in water at a pH preferably between about 7.0 to 7.6 pH, preferably pH 7.4±0.3. In another aspect of the invention, the compounds are formulated as suspensions. In a preferred embodiment, the formulation is in a 1% w/v ophthalmic suspension: 1.0% compound of formula V, micronized; 0.06% carbomer (carbopol 1382), NF; 1.0% poloxamer 188, NF; 2.5% glycerin, USP; 0.01% benzalkonium chloride, NF; sodium hydroxide, NF, q.s. pH 7.4±0.3; and purified water, USP (the formulation may be prepared as % w/w for convenience, and higher grades of water, USP, may be substituted). Various preservatives may be used in an ophthalmic preparation. Preservatives include, but are not limited to, benzalkonium chloride, chlorobutanol, thimerosal, phenylmercuric acetate, and phenylmercuric nitrate. Likewise, various vehicles may be used in such ophthalmic preparation. These vehicles include, but are not limited to, polyvinyl alcohol, povidone, cyclodextrins, hydroxypropyl methyl cellulose, poloxamers, carboxymethyl cellulose and hydroxyethyl cellulose. Such preservatives, if utilized, will typically be employed in an amount between about 0.001 and about 1.0 wt %.

Tonicity adjusters may be added as needed or convenient. They include, but are not limited to, salts, particularly sodium chloride, potassium chloride etc., mannitol and glycerin, or any other suitable ophthalmically acceptable tonicity adjuster. Such agents, if utilized, will typically be employed in an amount between about 0.1 and about 10.0 wt %.

Various buffers and means for adjusting pH may be used so long as the resulting preparation is ophthalmically acceptable. Accordingly, buffers include but are not limited to, acetate buffers, titrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to increase ocular absorption of the compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The ophthalmic solution (ocular drops) may be administered to the mammalian eye as often as necessary to maintain an acceptable level of intraocular pressure in the eye. In other words, the ophthalmic solution (or other formulation) is administered to the mammalian eye as often as necessary to maintain the beneficial effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye once daily. The formulations may be administered to the mammalian eye anywhere from about 1–4× daily, or as otherwise deemed appropriate by the attending physician. The formulations may also be administered in combination with one or more other pharmaceutical compositions known to reduce intraocular pressure in a subject or otherwise have a beneficial effect in a subject, including miotics (e.g., pilocarpine, carbachol, and acetylcholinesterase inhibitors); sympathomimetics (e.g., epinephrine and dipivalylepinephrine); beta-blockers (e.g., betaxolol, levobunolol and timolol); alpha-2 agonists (e.g., para-amino clonidine); carbonic anhydrase inhibitors (e.g., acetazolamide, methazolamide and ethoxzolamide); and prostaglandins and their analogs and derivatives (e.g., latanaprost).

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference.

As will likewise be appreciated by those skilled in the art, the compositions may be formulated in various dosage forms suitable for topical ophthalmic delivery, as described above, including solutions, suspensions, emulsions, gels, and erodible solid ocular inserts. The compositions are preferably aqueous suspensions or solutions. Further, such formulated compositions may also include one or more additional active ingredients in a single vial for delivery to the patient. That is to say, in addition to one or more potassium channel inhibitors present in a single formulation, the present invention additionally contemplates the presence of one or more of the following therewith: miotics (e.g., pilocarpine, carbachol, and acetylcholinesterase inhibitors); sympathomimetics (e.g., epinephrine and dipivalylepinephrine); beta-blockers (e.g., betaxolol, levobunolol and timolol); alpha-2 agonists (e.g., para-amino clonidine); carbonic anhydrase inhibitors (e.g., acetazolamide, methazolamide and ethoxzolamide); and prostaglandins and their analogs and derivatives (e.g., latanaprost) in a single formulation for administration. One skilled in the art will recognize due care will need to be given in selecting such agents for co-administration from a single formulation with due regard for chemical stability and compatibility with other agents (whether active therapeutic agents or excipients) in the composition made available to the patient.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to reduce sickle cell dehydration and/or delay the occurrence of erythrocyte sickling or distortion in situ, such compositions will contain an amount of active ingredient effective to achieve this result. Similarly, when the pharmaceutical composition is used to treat or prevent glaucoma, a therapeutically effective amount will reduce intraocular pressure below a predetermined pressure threshold. Determination of a therapeutically effective amount of a compound of the invention is well within the capabilities of those skilled in the art, especially in light of the detailed disclosure herein.

For any compound described herein, the therapeutically effective amount can be initially determined from cell culture assays. Target concentrations will be those concentrations of active compound(s) that are capable of inducing inhibition of the intermediate conductance, calcium activated potassium channel. In preferred embodiments, said channel activity is at least 25% inhibited. Concentrations of active compound(s) that are capable of inducing at least about 50%, 75%, or even 90% or higher inhibition of the ion channel potassium flux are presently preferred. The percentage of inhibition of the intermediate conductance, calcium activated potassium channel in the patient can be monitored to assess the efficacy of the drug concentration achieved, and the dosage can be adjusted upwards or downwards by the medical practitioner to achieve the desired percentage of inhibition.

As is well known in the art, therapeutically effective amounts for use in humans can also be determined from animal models. For example, a dose for humans can be formulated to achieve a concentration that has been found to be effective in animals. A particularly useful animal model for sickle cell disease is the SAD-1 mouse model (Trudel et al., *EMBO J.* 11: 31573165 (1991)). The dosage in humans can be adjusted by monitoring Gardos channel inhibition and adjusting the dosage upwards or downwards, as described above.

A therapeutically effective dose can also be determined from human data for compounds which are known to exhibit similar pharmacological activities, such as clotrimazole and other antimycotic agents (see, e.g., Brugnara et al., *JPET*273:266272 (1995)); Benzaquen et al., *Nature Medicine* 1: 534–540 (1995); Brugnara et al., *J. Clin. Invest.* 97(5): 1227–1234 (1996)). The applied dose can be adjusted based on the relative bioavailability and potency of the administered compound as compared with clotrimazole.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will generally not be of particular importance. In such instances, the compound is administered so as to achieve a concentration at the local area effective to achieve the intended result.

By way of example, when a compound of the invention is used in the prophylaxis and/or treatment of sickle cell disease, including both chronic sickle cell episodes and acute sickle cell crisis, a circulating concentration of administered compound of about 0.001 μM to 20 μM is considered to be effective, with about 0.01 μM to 5 μM being preferred.

Patient doses for oral administration of the compounds described herein, which is the preferred mode of administration for prophylaxis and for treatment of chronic sickle cell episodes, typically range from about 0.01 mg/day to about 100 mg/day, more typically from about 0.1 mg/day to about 10 mg/day, and most typically from about 0.50 mg/day to about 5 mg/day. Stated in terms of patient body weight, typical dosages range from about 0.0001 to about 0.150 mg/kg/day, more typically from about 0.001 to about 0.015 mg/kg/day, and most typically from about 0.01 to about 0.10 mg/kg/day.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v. In another embodiment, the dosage range is 10–1000 μg per eye. In another embodiment, the dosage range is 75–150 μg per eye.

For other modes of administration, dosage amount and interval can be adjusted individually to provide levels of the administered compound effective for the particular clinical indication being treated. For example, if acute sickle crises are the most dominant clinical manifestation, in one embodiment, a compound according to the invention can be administered in relatively high concentrations multiple times per day. Alternatively, if the patient exhibits only periodic sickle cell crises on an infrequent, periodic or irregular basis, in one embodiment, it may be more desirable to administer a compound of the invention at minimal effective concentrations and to use a less frequent administration regimen. This will provide a therapeutic regimen that is commensurate with the severity of the individual's sickle cell disease.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Compound Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

III. Methods for Decreasing Ion Flow in Intermediate Conductance, Calcium Activated Potassium Channels In addition to the compounds and pharmaceutical formulations discussed in detail above, the present invention provides a number of methods in which the compounds of the invention find use. The methods include, but are not limited to, those that are used in a laboratory setting to probe the basic mechanisms of intermediate conductance, calcium activated potassium channels and channel-active compounds, e.g., pharmacokinetics, drug activity, disease origin and progression and the like.

Thus, in another aspect, the invention provides a method of inhibiting potassium flux of a cell. The method comprises, contacting a cell with an effective amount of a compound of the invention.

This aspect of the invention has a wide range of uses, but it is preferred as a modality for the study of the basic mechanisms underlying potassium flux and the mechanism of activity of agents that modulate this flux. Further, the compounds of the invention can be utilized as tools in the discovery of new agents that modulate potassium flux. For example, the compounds of the invention can be utilized in assays, such as competitive assays, to test the efficacy of putative inhibitors of potassium flux. These methods of the invention can be performed both in vitro and in vivo. Assays according to the present invention can be carried out by, for example, modifying art-recognized methods to allow the incorporation of the compounds of the invention into them. Such modification is well within the skill of those of skill in the art.

The methods provided in this aspect of the invention are also useful for the diagnosis of conditions that can be treated by modulating ion flux through intermediate conductance, calcium activated potassium channels, or for determining if a patient will be responsive to therapeutic agents, which act by blocking potassium channels. In particular, a patient's cell sample can be obtained and contacted with a compound of the invention and the ion flux can be measured relative to a cell's ion flux in the absence of a compound of the invention. A decrease in ion flux will typically indicate that the patient will be responsive to a therapeutic regimen of ion channel openers.

IV. Methods for Treating Conditions Mediated by Intermediate Conductance, Calcium Activated Potassium Channels In another preferred embodiment, this method is used to treat or prevent a condition that can be positively affected by modulating potassium flux. In a presently preferred embodiment, the condition is sickle cell disease or glaucoma and inflammation. For example, in sickle cell disease, the invention provides a method for reducing erythrocyte dehydration. This method comprises, contacting an erythrocyte with an effective amount of a compound of the invention. This aspect of the invention can be used for a range of purposes including, for example, study of the mechanism of erythrocyte dehydration, investigation of compounds that inhibit or reverse erythrocyte dehydration and the treatment or prevention of conditions associated with erythrocyte dehydration.

In another aspect, the invention provides a method of treating or preventing sickle cell disease. The method comprises administering to a subject suffering sickle cell disease a therapeutically effective amount of one or more compounds of the invention with or without one or more other agents useful in ameliorating the effects of the disease. This aspect of the invention can be utilized to prevent the onset of acute sickle cell events or to ameliorate the effects of these events. Further, the method can be used to treat and/or prevent chronic sickle cell disease. The method can make use of the compounds of the invention per se or, preferably, the pharmaceutical formulations of the invention. The relevant modes of administration, choice of dosage levels and frequency of dosing are discussed above.

The following examples are provided by way of illustration only and not by way of limitation. Those of skill in the art will readily recognize a variety of non-critical parameters that can be changed or modified to yield similar results.

EXAMPLES

Examples 1–3 illustrate methods for the synthesis and characterization of compounds of the invention. The compounds of the invention were isolated in substantially pure form utilizing the methods detailed in these Examples.

Example 4 illustrates the use of a rubidium flux assay to determine the activity of the compounds of the invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: rt (room temperature ~25° C.), mp (melting point), L (liter(s)), mL (milliliters), mmol (millimoles), g (grams), mg (milligrams), min (minutes), and h (hours).

Example 1

1.1 2-(3-trifluoromethyl-benzenesulfonylamino)-cyclohex-1-enecarboxylic Acid Methyl ester (31)

3-Trifluoromethylsulfonyl chloride (544 μL, 3.4 mmol) was added drop wise to a stirring solution of 2-amino-cyclohex-1-enecarboxylic acid methyl ester (530 mg, 3.4 mmol) in pyridine (4 mL). After 18 h at rt the solvent was removed under reduced pressure. Column chromatography (hexane/ethyl acetate; 3:1) gave the desired product as a colorless oil which solidified upon standing (524 mg, 42%); $^1$H NMR δ ($CDCl_3$) 11.70 (s, 1H), 8.14 (s, 1H), 8.06 (d, J=7.8 Hz, 1H), 7.82 (d, J=7.7 Hz, 1H), 7.68 (t, J=7.8 Hz, 1H), 3.77 (s, 3H), 2.43-2.40 (m, 2H), 2.25-2.22 (m, 2H), 1.56-1.50 (m, 4H); MS (EI) found (M+1) 364.4.

1.2 N-(2-furan-2-yl-phenyl)-3-trifluoromethyl-benzenesulfonamide (76)

Scheme 1

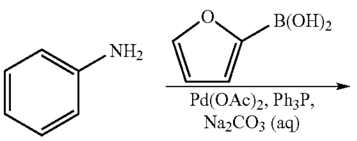

-continued

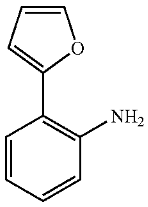

(A)

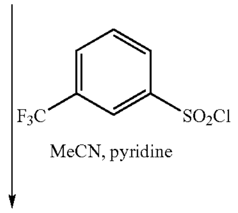

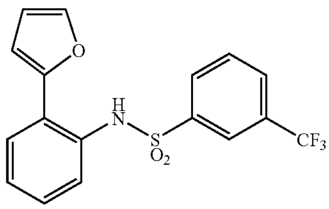

76

2-Iodoaniline (200 mg, 0.913 mmol) and furan-2-boronic acid (107 mg, 0.959 mmol) were combined in 2 mL of ethanol and stirred for 30 minutes. Palladium acetate (6 mg, 0.03 mmol), triphenylphosphine (22 mg, 0.82 mmol) and a 2N aqueous solution of sodium carbonate (0.57 mL, 1.1 mmol) were added to the reaction mixture successively. The reaction was heated to 75° C. and stirred for 5 h. It was then cooled to 55° C. and stirred for another 14 h. After cooling the reaction mixture to room temperature, water (5 mL) was added and the mixture was extracted with ethyl acetate (2×10 mL). The organic layers were combined and dried ($Na_2SO_4$). Column chromatography (hexanes/ethyl acetate; 9:1) gave the desired product (A) as a white solid (73 mg, 50%): $^1$H NMR δ ($CDCl_3$) 7.50 (d, J=1.0 Hz, 1H), 7.48 (dd, J=1.4, 7.7 Hz, 1H), 7.12 (dt, J=1.4, 7.7 Hz, 1H), 6.80 (t, J=7.1 Hz, 1H), 6.75 (d, J=8.0 Hz, 1H), 6.59(d, J=3.3 Hz, 1H), 6.51 (dd, J=1.9, 3.3 Hz, 1H).

A solution of 3-trifluoromethylsulfonyl chloride (42 mg, 0.17 mmol) and pyridine (38 μL, 0.47 mmol) in acetonitrile (2 mL) was added to a solution 2-furan-2-yl-phenylamine (A) (25 mg, 0.16 mmol) in acetonitrile (0.5 mL). After 18 h a saturated aqueous solution of sodium bicarbonate (5 mL) was added and the mixture was extracted with ethyl acetate (2×10 mL). The organic layers were combined and dried ($Na_2SO_4$). Column chromatography (hexanes/ethyl acetate; 9:1) gave the desired product (76) as a white solid (40 mg, 70%). $^1$H NMR δ ($CDCl_3$) 7.89 (s, 1H), 7.62 (m, 4H), 7.35 (m, 4H). 7.24 (m, 1H), 6.35 (dd, J=1.8, 3.4 Hz, 1H), 6.21 (d, J=3.4 Hz, 1H).

1.3 N-[2-(3-methyl-[1,2,4]oxadiazol-5-yl)-phenyl]-3-trifluoromethyl-benzenesulfonamide (82)

Scheme 2

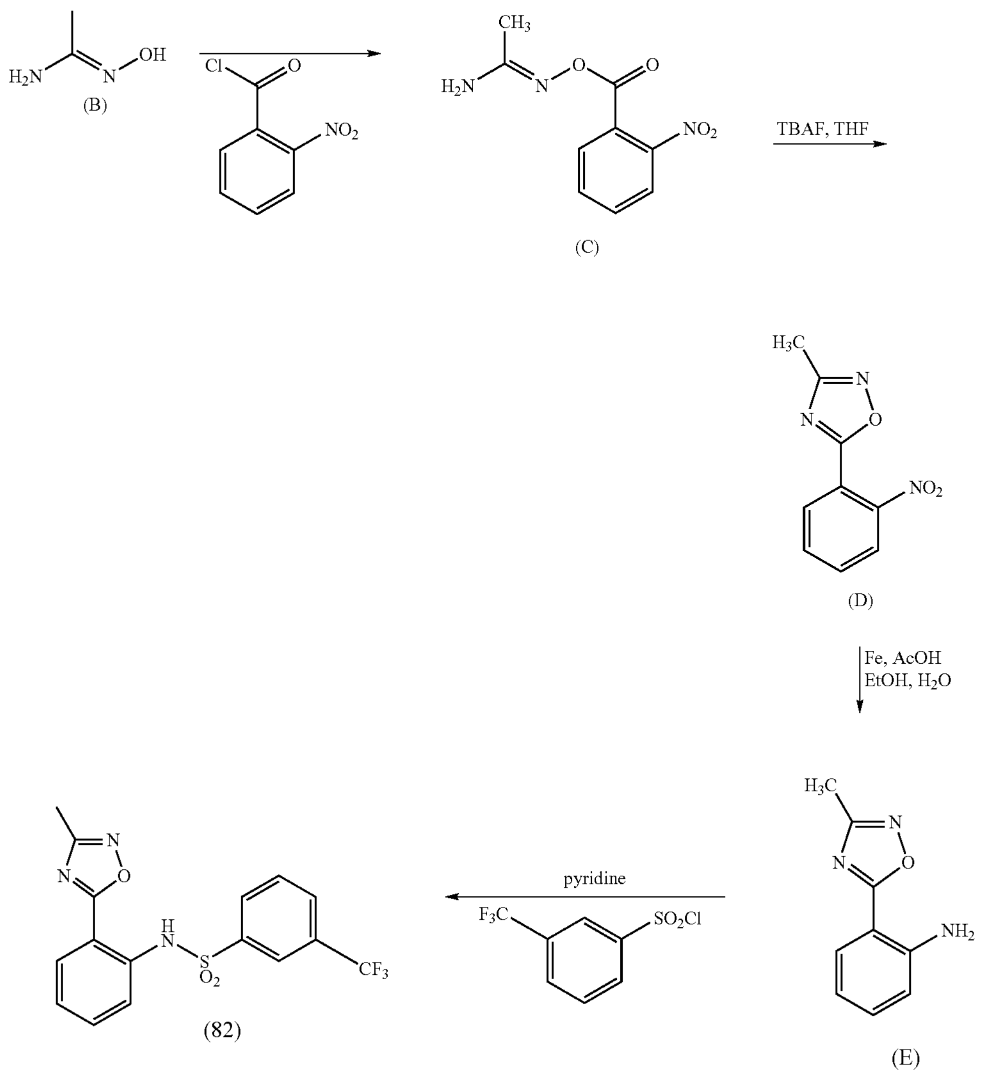

(B) (C) (D) (E) (82)

Acetonitrile (0.10 mL, 2.0 mmol) and hydroxylamine (0.49 mL, 8.0 mmol) were combined in ethanol (10 mL). The mixture was heated to 60° C. for 3 h. After cooling to room temperature, all solvents were removed to yield the crude amidine (B) as a white solid. The crude amidine (B) and diisopropylethylamine (0.70 mL, 4.0 mmol) were combined in dichloromethane (10 mL) and stirred for 30 min. A solution of 2-nitrobenzoyl chloride (0.32 mL, 2.4 mmol) in dichloromethane (2 mL) was slowly added to the reaction mixture. After 18 h, water (5 mL) was added to the mixture and the organics were extracted with dichloromethane (2×5 mL), combined and dried ($Na_2SO_4$). Recrystallization from ethyl acetate and hexanes gave (C) as a yellow solid as a mixture of E- and Z-isomers (440 mg, 98%): $^1H$ NMR δ ($CDCl_3$) 7.93 (dd, J=1.3, 7.8 Hz, 1H), 7.83 (dd, J=1.5, 7.6 Hz, 1H), 7.74–7.62 (m, 2H), 4.78 (broad s, 2H), 2.01 (s, 3H).

A 1.0 M solution of tetrabutylammonium fluoride in tetrahydrofuran (0.66 mL, 0.66 mmol) was added to a solution of compound (C) (440 mg, 1.97 mmol) in tetrahydrofuran (5 mL). The reaction mixture was stirred for 18 h after which water (5 mL) was added. The organics were extracted with ethyl acetate (2×5 mL), combined and dried ($Na_2SO_4$). Column chromatography (hexanes/ethyl acetate; 4:1) gave (D) as an off-white solid (386 mg, 95%): $^1H$ NMR δ ($CDCl_3$) 7.99 (m, 1H), 7.93 (m, 1H), 7.77 (m, 2H), 2.50 (s, 3H).

Compound (D) (100 mg, 0.487 mmol) and glacial acetic acid (0.12 mL, 2.1 mmol) were dissolved in 1.5 mL of water and 3.0 mL of ethanol and then heated at reflux. The reaction vessel was removed from the bath to allow it to cool slightly and iron (109 mg, 1.95 mmol) was added in portions. The reaction mixture was again heated at reflux for 20 min after which the reaction was cooled to room temperature and basified with 30% aqueous ammonium hydroxide solution to a pH~9. The mixture was filtered through Celite and the ethanol was removed by rotary evaporation. The residue was extracted with ethyl acetate (2×5 mL) and dried ($Na_2SO_4$). Column chromatography (hexanes/ethyl acetate; 4:1) gave (E) as a beige solid (39 mg, 46%). $^1$H NMR δ ($CDCl_3$) 7.91 (d, J=7.1 Hz, 1H), 7.30 (dd, J=1.4, 8.0 Hz, 1H), 6.76 (m, 2H), 2.46 (s, 3H).

Compound (82) was prepared as described in the procedure of (76) using compound (E) (30 mg, 0.17 mmol) as the aniline. Purification was accomplished by column chromatography using 5:1 hexanes:ethyl acetate as the eluent. This yielded the desired product (33 mg, 50%) as an off white solid.

1.4 N-[4,5-dimethoxy-2-(3-methyl-[1,2,4]oxadiazol-5-yl)-phenyl]-3-trifluoromethyl-benzenesulfonamide (41)

nitrobenzoic acid (585 mg, 2.57 mmol) with oxalyl chloride (0.36 mL, 4.1 mmol) in dichloromethane using N,N-dimethylformamide as a catalyst. The resulting mixture was stirred at room temperature for 1 h, the volatile liquids were removed and the resulting acid chloride was used without further purification.

Purification of (F) was accomplished by column chromatography using 1:4 hexanes:ethyl acetate followed by 100% ethyl acetate. This yielded (F) as a mixture of E- and Z-isomers (397 mg, 73%): $^1$H NMR δ ($CDCl_3$) for the E-isomer 7.70 (s, 1H), 7.08 (s, 1H), 4.83 (broad s, 2H), 4.11 (s, 6H), 2.92 (s, 3H) and for the Z-isomer 7.46 (s, 1H), 7.16 (s, 1H), 4.82 (broad s, 2H), 3.98 (s, 6H), 2.00 (s, 3H).

Scheme 3

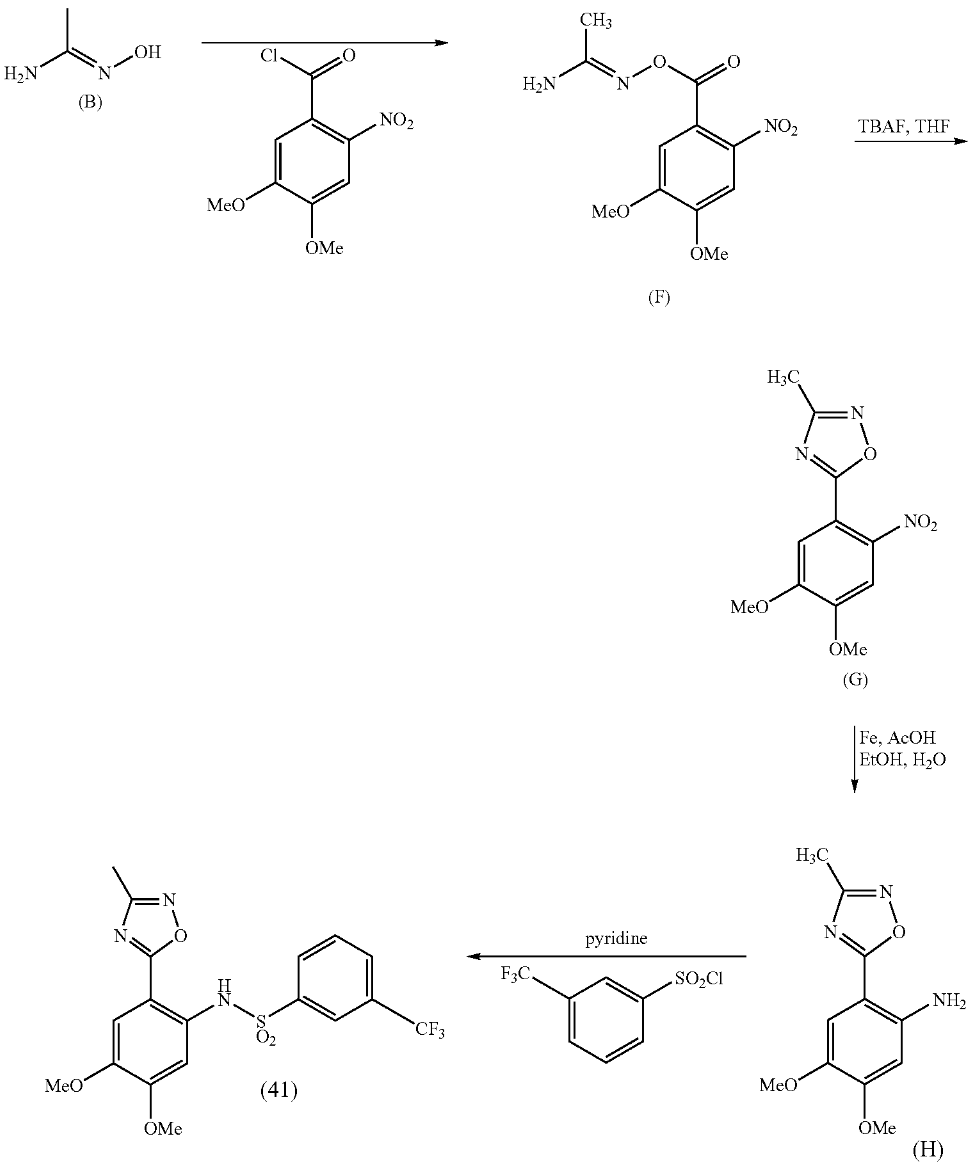

Compound (F) was prepared as described in the procedure of compound (C). The 3,4-dimethoxy-5-nitrobenzoyl chloride was prepared by the reaction of 3,4-dimethoxy-5-

Compound G was prepared as described in the procedure of compound (D). Purification was accomplished using 1:1 hexanes:ethyl acetate as the eluent. This gave the desired product as a yellow solid (281 mg, 76%): $^1$H NMR δ (CDCl$_3$) 7.58 (s, 1H), 7.18 (s, 1H), 4.02 (s, 3H), 4.00 (s, 3H), 2.49 (s, 3H).

1.5 N-[2-(3-methoxy-[1,2,4]oxadiazol-5-yl)-phenyl]-3-trifluoromethyl-benzenesulfonamide (83)

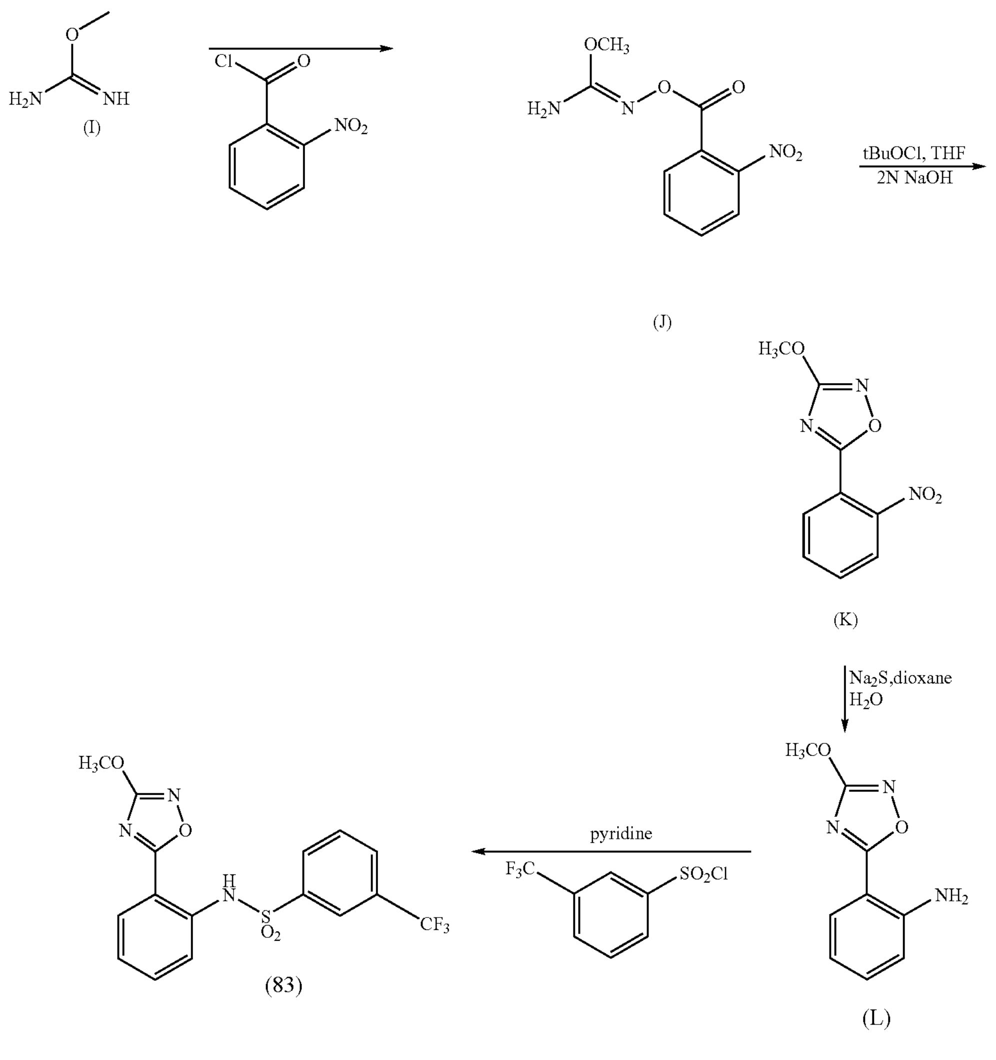

O-Methylisourea hydrochloride (I) (553 mg, 5.00 mmol) was added to cooled (0° C.) 2N aqueous sodium hydroxide (7.0 mL, 14 mmol). 2-Nitrobenzoyl chloride (0.66 mL, 5.0 mmol) was slowly added to the reaction mixture. After 1.5 h the organics were extracted with ethyl acetate (2×10 mL), combined and dried (Na$_2$SO$_4$). Removal of the solvent by rotary evaporation gave crude (J) (776 mg, 70%) as a white solid. $^1$H NMR δ (CDCl$_3$) 9.03 (broad s, 1H), 7.94 (dd, J=1.6, 7.5 Hz, 1H), 7.74–7.50 (m, 3H) 5.73 (broad s, 1H), 3.83 (s, 3H).

Compound (J) (250 mg, 1.12 mmol) was suspended in ether (3 mL) and cooled to 0° C. A solution of tert-butyl hypochlorite (0.14 mL, 1.2 mmol) in ether (0.5 mL) was then slowly added. The mixture was stirred for 30 minutes. A 2N aqueous sodium hydroxide solution was added and the reaction mixture was warmed to room temperature and was stirred for 1 hour. The ether was removed by rotary evaporation and methanol (2 mL) was added. The solution was then warmed to 60° C. for 5 hours and then cooled to room temperature. The resulting solution was extracted with ethyl acetate (2×5 mL). The organic layers were combined and dried (Na$_2$SO$_4$). Purification was accomplished by column chromatography using 8:1 and then 1:1 hexanes:ethyl acetate as the eluent. Compound (K) was obtained as a white solid (89 mg, 36%). $^1$H NMR δ (CDCl$_3$) 8.00 (m, 1H), 7.90 (m, 1H), 7.76 (m, 2H), 4.12 (s, 3H).

Compound (K) (89 mg, 0.402 mmol) was dissolved in dioxane (1 mL). In a separate vessel, sodium sulfide (242 mg, 1.01 mmol) was dissolve in water (1 mL). Both solutions were heated at 80° C. and the aqueous solution was added to the dioxane solution. After 20 minutes the reaction was cooled to room temperature. The organics were extracted with EtOAc (3×10 mL), combined and dried (Na$_2$SO$_4$). Purification of the resulting residue by column chromatography (hexanes:ethyl acetate; 8:1) gave compound (L) as a white solid (52 mg, 67%). $^1$H NMR δ

($CDCl_3$) 7.88 (dd, J=1.6, 8.4 Hz, 1H), 7.31 (dt, J=1.6, 7.8 Hz, 1H), 6.75 (m, 2H), 4.11 (s, 3H); MS (EI) found (M+1) 192.1.

A 0.3 mL solution of 3-(trifluoromethyl)sulfonyl chloride (37 mg, 0.15 mmol) in acetonitrile (1 mL) was added to a solution of (L) (26 mg, 0.14 mmol) and pyridine (33 μL, 0.41 mmol) in acetonitrile (0.5 mL) and the resulting solution was stirred for 15 h. The mixture was diluted with ethyl acetate (5 mL), washed with 1 N hydrochloric acid and dried ($Na_2SO_4$). Purification by column chromatography (hexanes: ethyl acetate; 10:1) yielded the desired product (83) as a white solid (12 mg, 22%). $^1H$ NMR δ ($CDCl_3$) 10.36 (s, 1H), 8.11 (s, 1H), 7.96 (dd, J=1.6, 7.0 Hz, 1H), 7.80 (d, J=8.3 Hz, 1H), 7.75 (d, J=7.3 Hz, 1H), 7.54 (m, 2H), 7.22 (t, J=8.2 Hz, 1H), 4.13 (s, 3H); MS (EI) found (M+1) 399.9.

Example 2

2.1 General Procedure for the Preparation of Oxazole Functionalized Bisaryl Sulfonamides As shown in Scheme 5, a solution of acid chloride (M) (1 eq) in DCM was added slowly to a stirring solution of 1,2,3-triazole (1 eq) and Hunigs base (1.2 eq) in DCM at rt. After TLC had shown conversion was complete the solution was washed with water (5 mL/1 mmol) and the organic layer dried ($Na_2SO_4$). The solvent was removed under reduced pressure. The crude material was dissolved in sulfalone (5 mL/1 mmol) and heated to 180–200° C. for 2–10 h. The solution was diluted with water (15 mL/1 mmol) and the product (N) was extracted with diethyl ether (2×5 mL/1 mmol). The organic layers were combined and dried ($Na_2SO_4$). Selective reduction of the nitro group over other substituents could be accomplished using one or more of the methods highlighted in scheme 5. Coupling of anilines (O) with arylsulfonyl chlorides was achieved using pyridine in acetonitrile at either ambient or elevated temperatures. Oxazole substituted bisaryl sulfonamides (P) were isolated in yields of about 20–60%.

Scheme 5

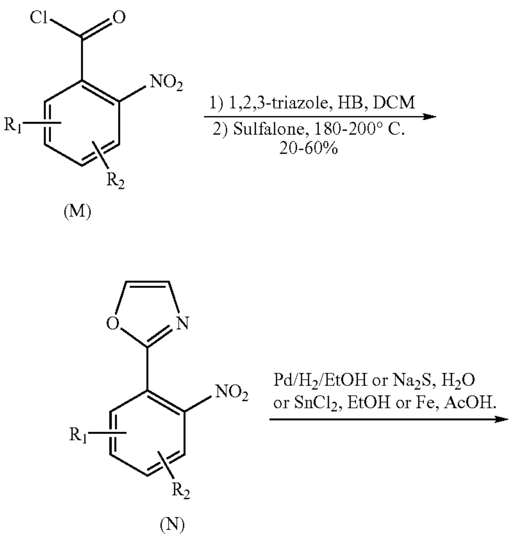

-continued

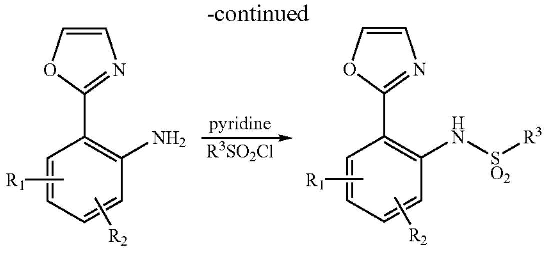

(O) (P)

2.2 N-(4-Methyl-2-oxazol-2-yl-phenyl)-3-trifluoromethyl-benzenesulfonamide (77)

$^1H$ NMR δ ($d_6$-DMSO) 11.17 (s, 1H), 8.24 (s, 1H), 7.93 (t, J=7.3 Hz, 2H), 7.86 (s, 1H), 7.71–7.67 (m, 2H), 7.52–7.48 (m, 2H), 7.33–7.30 (m, 1H), 2.28 (s, 3H); MS (EI) found (M+1) 383.4.

2.3 N-(2-Oxazol-2-yl-phenyl)-3-trifluoromethyl-benzenesulfonamide (74)

$^1H$ NMR δ ($d_6$-DMSO) 11.57 (s, 1H), 8.08 (s, 1H), 7.94 (d, J=7.7 Hz, 1H), 7.87 (d, J=7.7 Hz, 1H), 7.75 (d, J=8.0 Hz, 1H), 7.70–7.67 (m, 2H), 7.48 (t, J=7.8 Hz, 1H), 7.39 (t, J=7.7 Hz, 1H), 7.28 (s, 1H), 7.14 (t, J=7.6 Hz, 1H); MS (EI) found (M+1) 369.4.

2.4 N-(4-Methoxy-2-oxazol-2-yl-phenyl)-3-trifluoromethyl-benzenesulfonamide (40)

$^1H$ NMR δ ($CDCl_3$) 10.93 (s, 1H), 7.96 (s, 1H), 7.80 (d, J=7.8 Hz, 1H), 7.72 (d, J=9.1 Hz, 1H), 7.65–7.63 (m, 2H), 7.41 (t, J=7.8 Hz, 1H), 7.32 (d, J=3.0 Hz, 1H), 7.24 (s, 1H), 6.97 (dd, J=3.0 and 9.0 Hz, 1H), 3.81 (s, 3H); MS (EI) found (M+1) 399.4.

Example 3

3.1 General Procedure for the Preparation of Aryl Benzylsulfones

Scheme 6

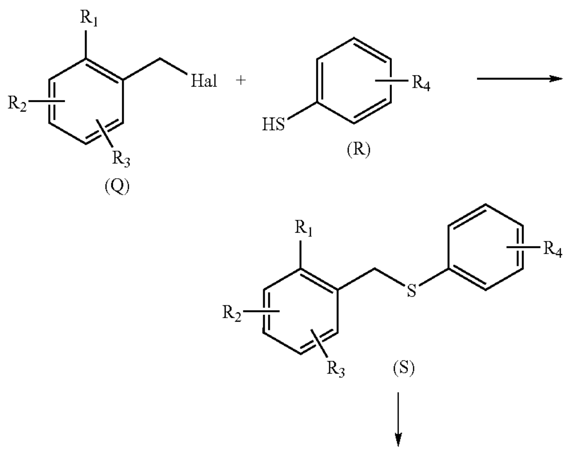

-continued

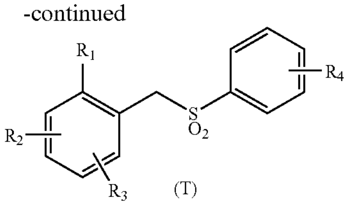

(T)

Thioethers of type (S) were prepared by reacting thiophenols with functionalized benzyl bromides (prepared either from toluoyl derivatives by bromination or by functionalization of commercially available benzyl bromides) using $K_2CO_3$ in DMSO at room temperature. Oxidation of the thioethers (S) using mCPBA afforded the corresponding sulfones (T) in high yield.

3.2 2-(3-Trifluoromethyl-phenylsulfanylmethyl)-benzoic Acid Methyl Ester (96)

$^1$H NMR δ ($CDCl_3$) 7.96 (dd, J=1.6 and 7.7 Hz, 1H), 7.50 (s, 1H), 7.44–7.21 (m, 5H), 7.19 (d, J=6.2 Hz, 1H), 4.56 (s, 2H), 3.89 (s, 3H); MS (EI) found (M+1) 327.4.

3.3 2-(3-Trifluoromethyl-benzenesulfonylmethyl)-benzoic Acid Methyl Ester (95)

$^1$H NMR δ ($CDCl_3$) 7.88 (dd, J=1.0 and 7.5 Hz, 1H), 7.83 (d, J=7.2 Hz, 1H), 7.80 (s, 2H), 7.58 (t, J=7.8 Hz, 1H), 7.50 (dd, J=1.2 and 7.5 Hz, 1H), 7.43 (dt, J=1.2 and 7.5 Hz, 1H), 7.36 (d, J=7.5 Hz, 1H), 5.11 (s, 2H), 3.71 (s, 3H); MS (EI) found (M+1) 359.6.

Example 4

Example 4 describes a bioassay for measuring the inhibition of a calcium activated potassium channel, the Gardos channel, in red blood cells by the compounds of the invention.

4.1 Materials and Methods

Heparinized whole blood was washed three times with Modified Flux Buffer (MFB: 140 mM NaCl; 5 mM KCl; 10 mM Tris; 0.1 mM EGTA; pH=7.4). Red blood cells ("RBCs") at an approximate 10% hematocrit. Washed cells were then incubated for 3 hours with $^{86}$Rb (5 μCi/mL). After this incubation period, the RBCs were washed three times with cold MFB. Washed $^{86}$Rb loaded RBCs were then incubated with a test compound of the invention for 10 minutes. $^{86}$Rb flux was then initiated by the addition of 10 μL/mL of a MFB solution containing 10 mM $CaCl_2$ and 100 μM A23187, a calcium ionophore. This yielded a final concentration of 100 μM $CaCl_2$ and 10 μM A23187 n the incubation medium. Cells were incubated for 10 minutes, spun down and the supernatant was removed. Samples were counted in a Wallace Microbeta liquid scintillation counter by Cerenkov emission. Total RBC $^{86}$Rb content was determined by lysing the RBCs with water and then precipitating protein using a 50:50 mixture of ethanol:chloroform. After a 20 minute microfuge spin, the aqueous and organic layers separated and the aqueous layer was removed and counted. Efflux is expressed as a percentage of the initial cell content of $^{86}$Rb.

4.2 Results

The above-described bioassay demonstrated that the compounds of the invention are excellent inhibitors of the Gardos channel. Results for the inhibition studies are displayed in Table 1, supra.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the structure:

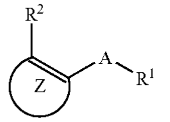

wherein ring system Z is a member selected from the group consisting of substituted or unsubstituted aryl, and substituted or unsubstituted $C_5$–$C_7$ carbocycle;

A is a member selected from —$NHS(O)_2$—, —$S(O)_2NH$—, —$C(R^4R^5)S(O)_n$—, —$S(O)_nC(R^4R^5)$—, —$C(R^4R^5)NHS(O)_n$—, —$S(O)_nNHC(R^4R^5)$—, —$C(R^4R^5)S(O)_nNH$—, and —$HNS(O)_nC(R^4R^5)$— wherein n is selected from the integers from 0 to 2;

$R^1$ is a member selected from the group of substituted or unsubstituted aryl, and substituted or unsubstituted ($C_5$–$C_7$)carbocycle;

$R^2$ is a member selected from substituted or unsubstituted 2-furan, substituted or unsubstituted 2-thiazole and

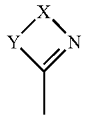

wherein

X is selected from the group consisting of —N═N—, —N═C($R^4$)—, —C($R^4$)═N—, —C($R^4R^5$)—C($R^4R^5$)— and —C($R^4$)═C($R^5$)—, wherein $R^4$ and $R^5$ are members independently selected from the group consisting of hydrogen, substituted and unsubstituted lower alkyl, —$OR^6$ and —$CF_3$ wherein $R^6$ is a member selected from hydrogen, and substituted or unsubstituted lower alkyl;

Y is O.

2. The compound according to claim 1, wherein Z is substituted or unsubstituted phenyl.

3. The compound according to claim 1, wherein $R^2$ is a member selected from substituted or unsubstituted 2-furan, and

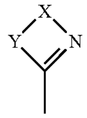

wherein

X is a member selected from the group consisting of —N=C($R^4$)—, —C($R^4$)=N—, —C($R^4R^5$)—C($R^4R^5$)— and —C($R^4$)=C($R^5$)—; and Y is O.

4. The compound according to claim 1, wherein $R^1$ is:

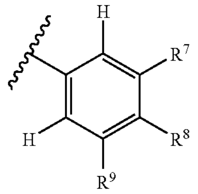

wherein $R^7$, $R^8$ and $R^9$ are members independently selected from the group consisting of H, halogen, substituted or unsubstituted $C_1$–$C_4$ alkyl, $OR^{10}$, —$CF_3$, and $NO_2$; and $R^{10}$ is a member selected from the group consisting of H, lower alkyl, substituted lower alkyl and —$CF_3$.

5. The compound according to claim 4, wherein $R^1$ is:

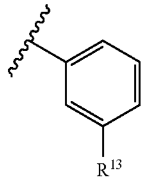

wherein $R^{13}$ is a member selected from halogen, substituted or unsubstituted $C_1$–$C_4$ alkyl, $CF_3$ and $OCF_3$.

6. The compound according to claim 1, having a structure selected from the group consisting of:

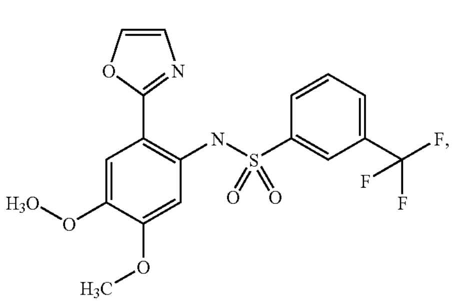

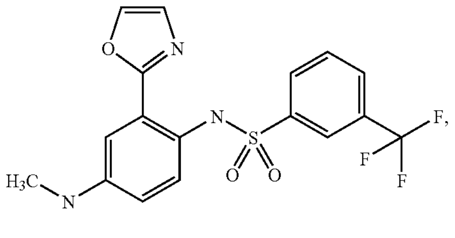

-continued

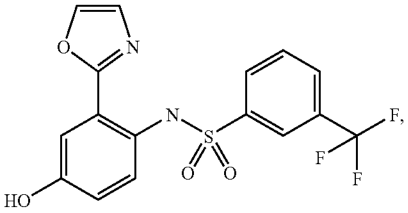

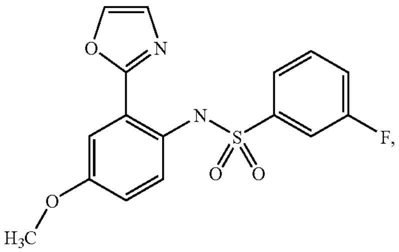

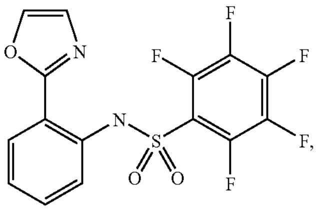

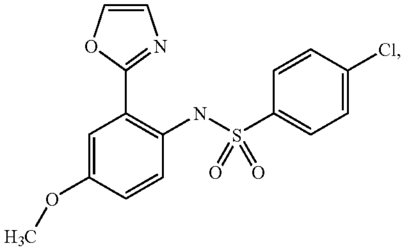

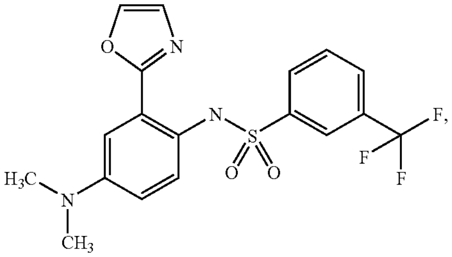

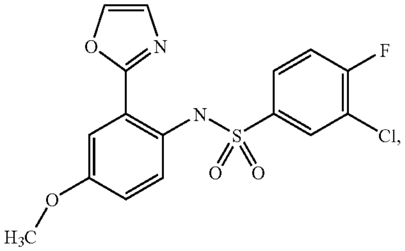

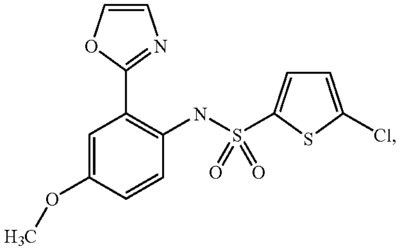

-continued
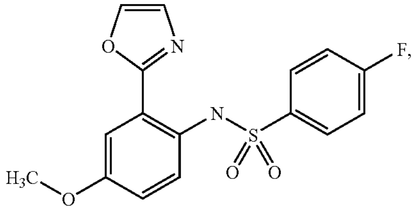
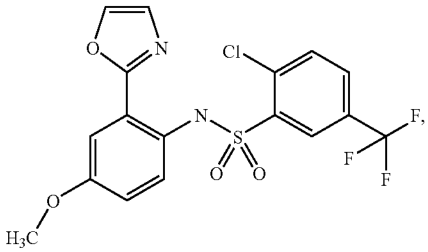
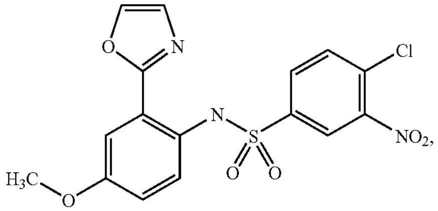
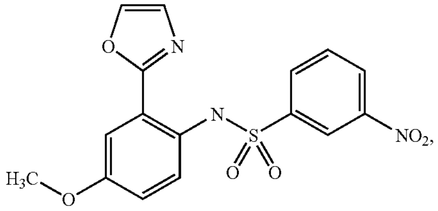
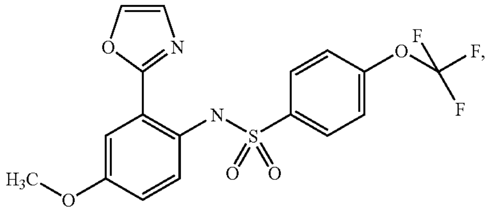
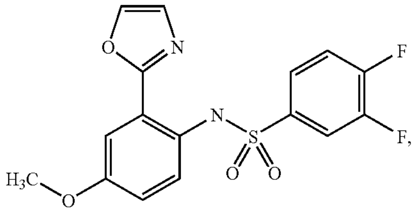
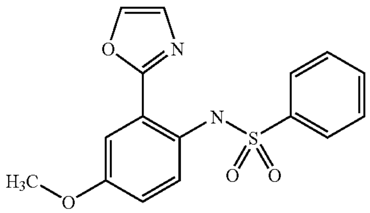
,
-continued
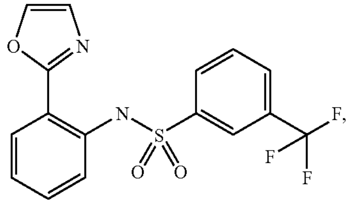
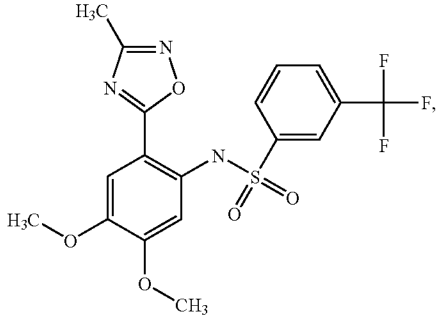
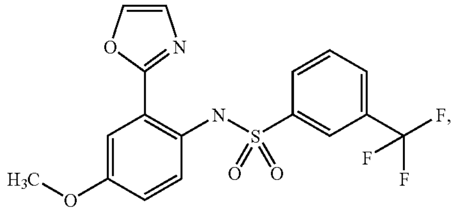
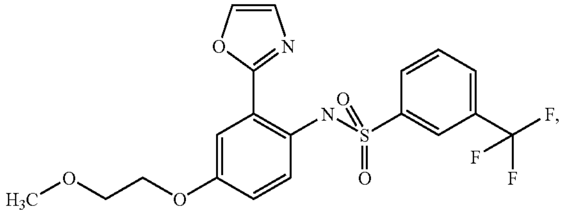
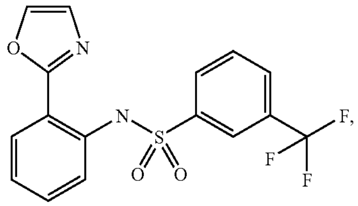
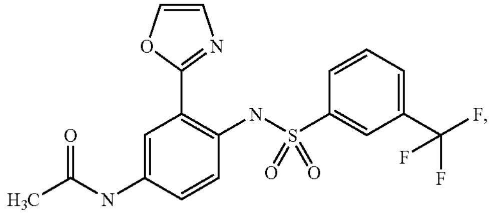
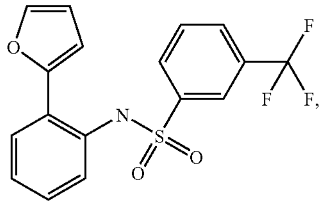

-continued
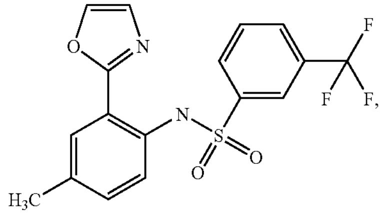
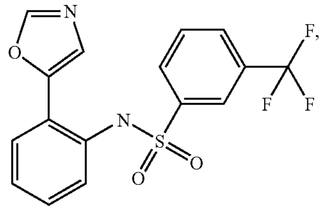
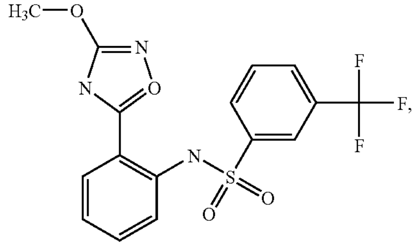
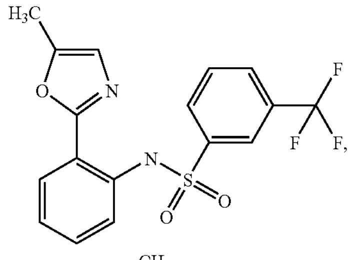
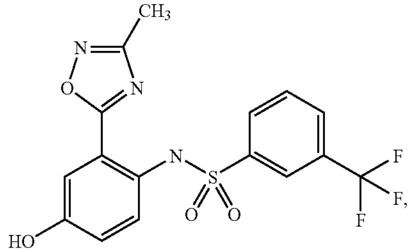
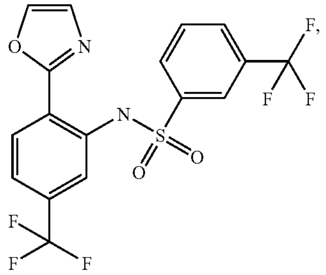
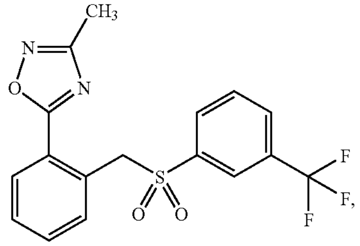
-continued
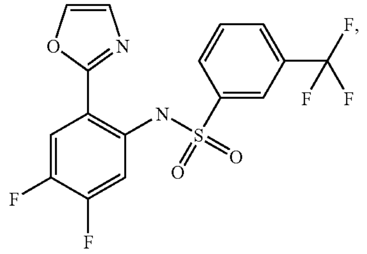
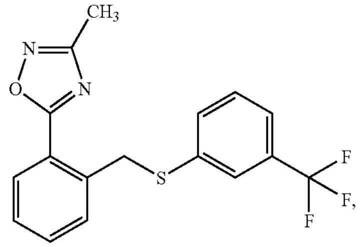
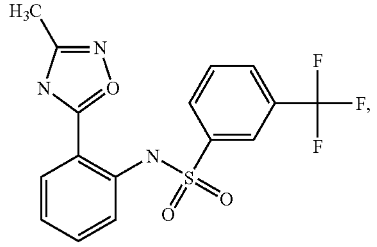
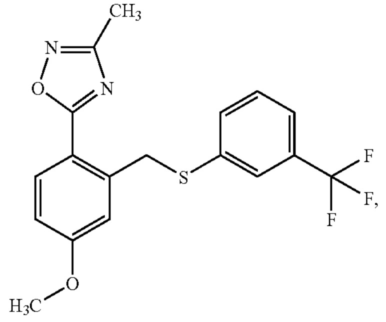
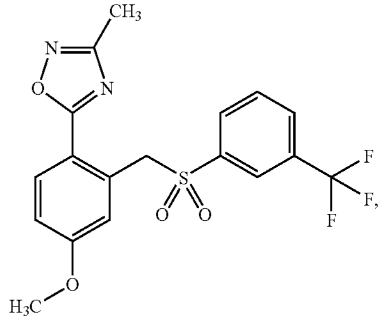
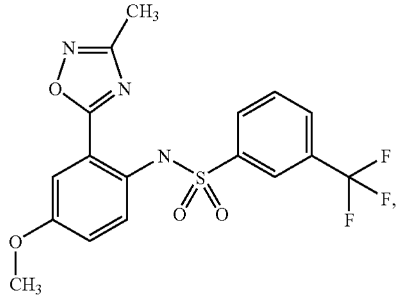

-continued
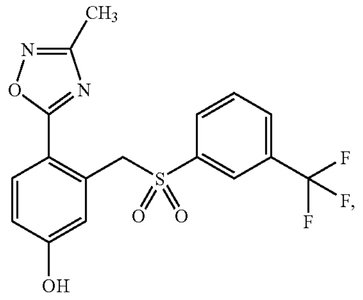
,
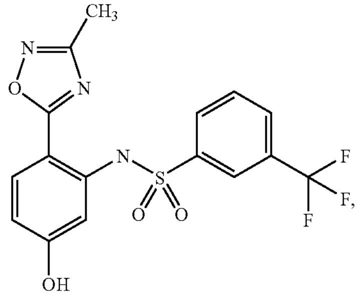
,
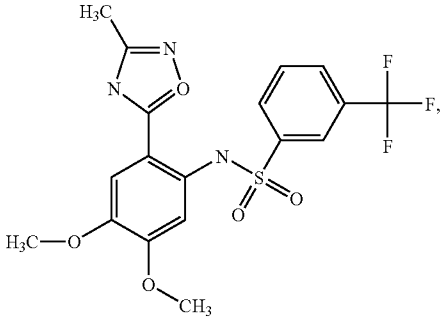
,
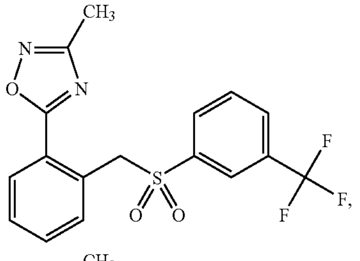
,
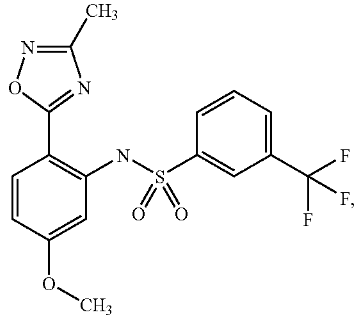
,
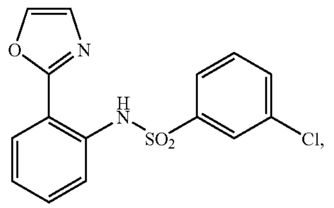
,
-continued
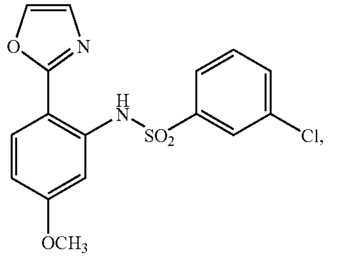
,
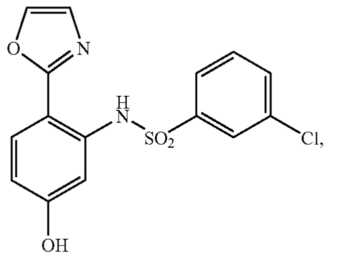
,
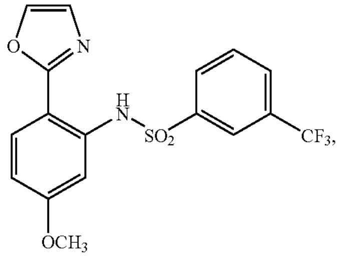
,
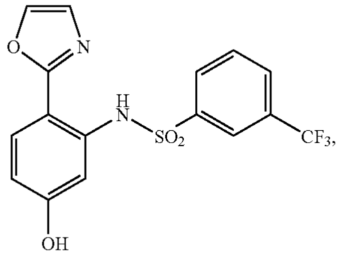
,
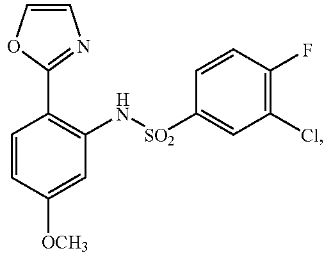
,
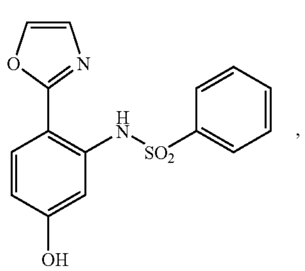
, -continued
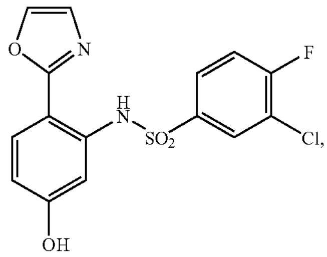
,
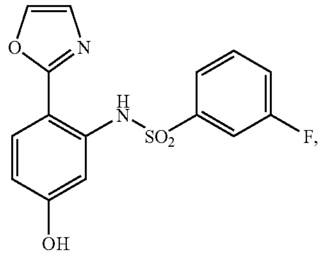
,
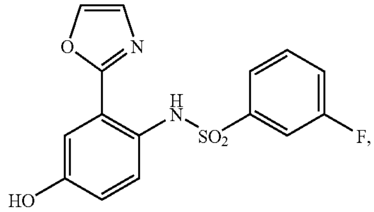
,
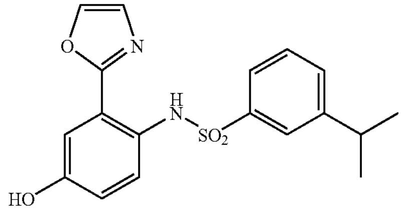
,
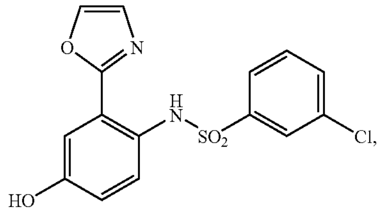
,
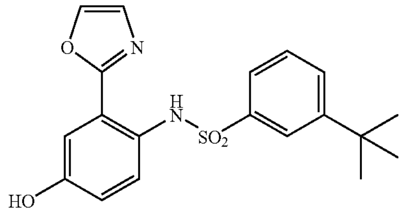
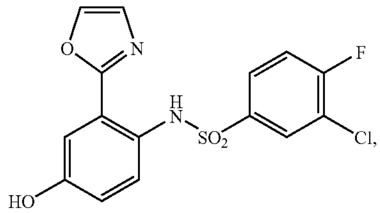
,
-continued
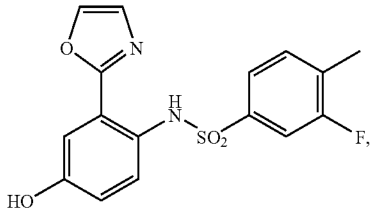
,
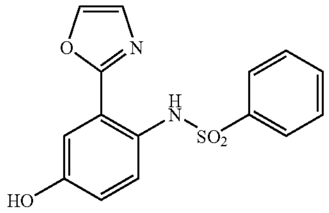
,
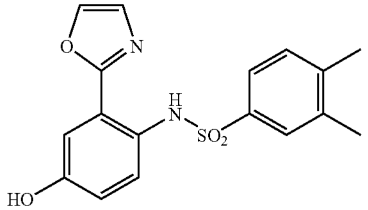
,
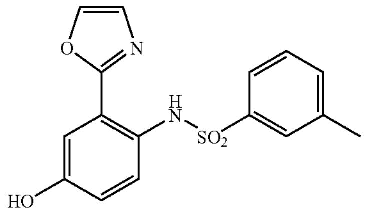
,
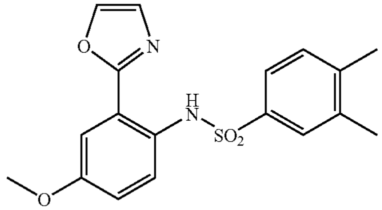
,
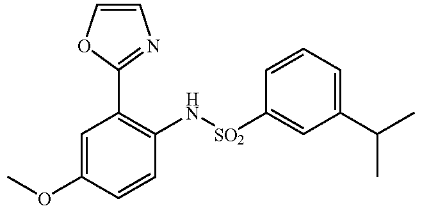
,
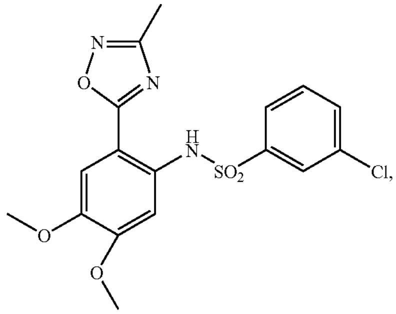
, -continued
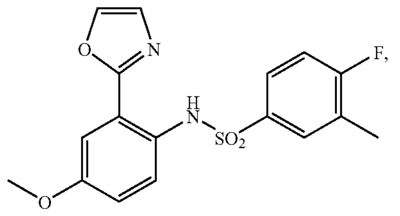
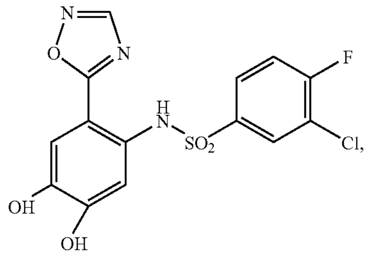
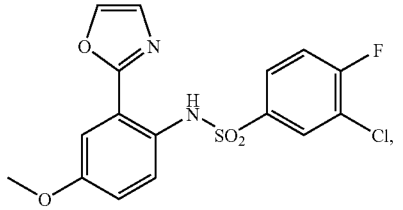
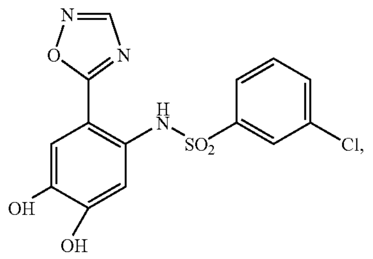
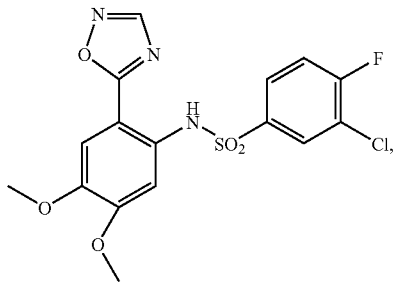
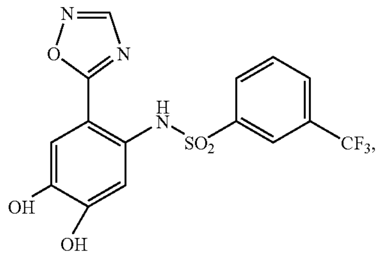
-continued
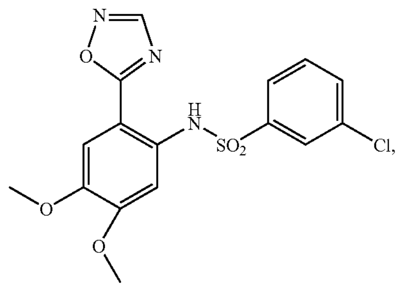
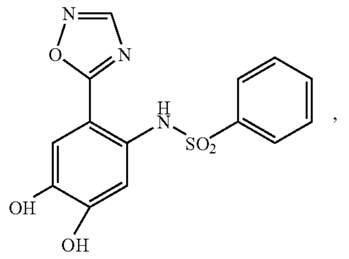
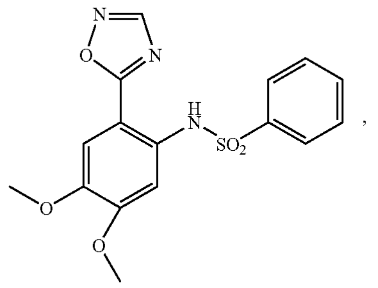
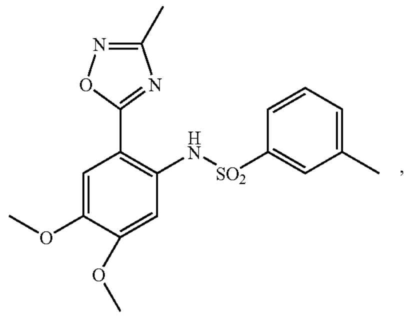
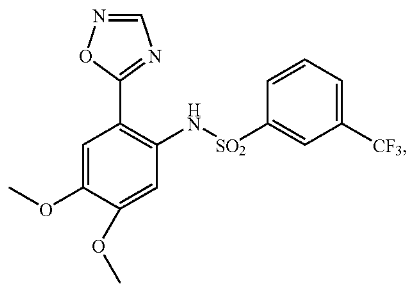

-continued
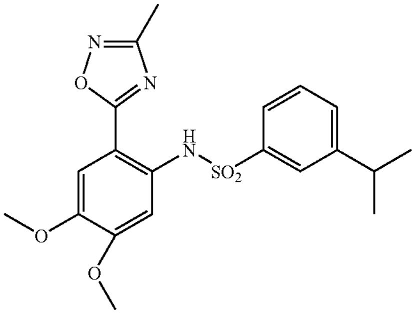
,
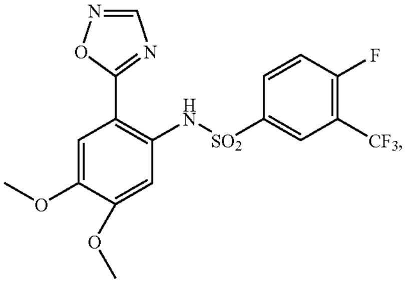
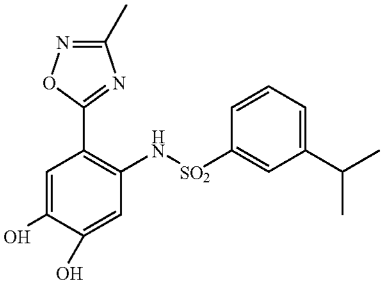
,
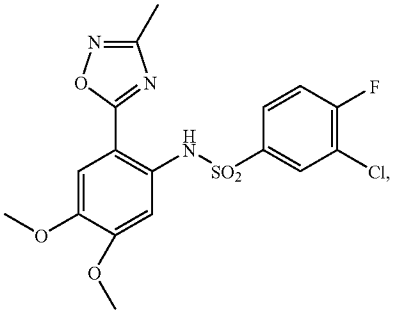
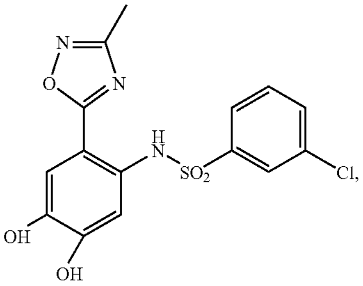
-continued
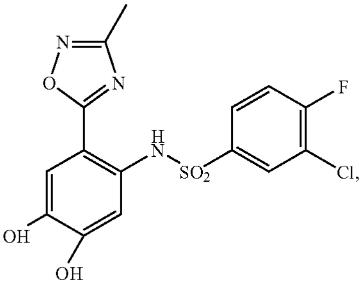
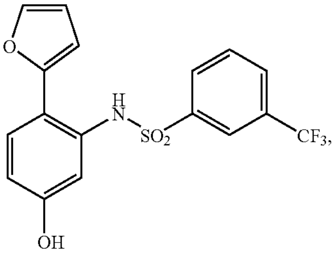
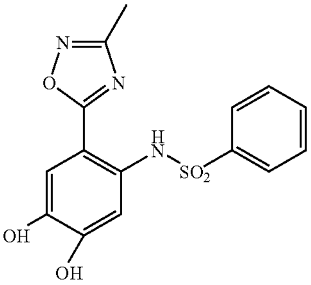
,
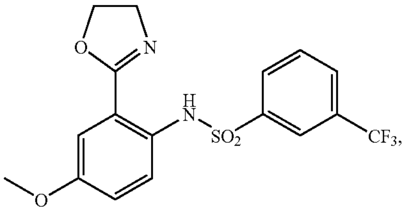
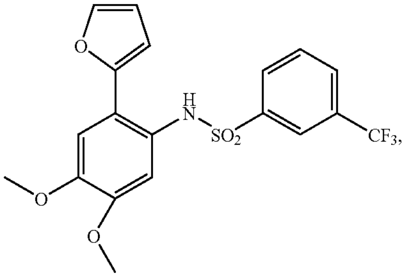
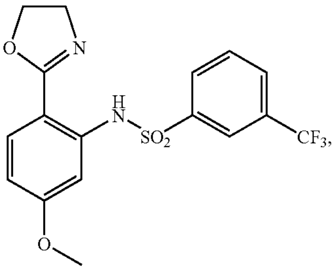

-continued

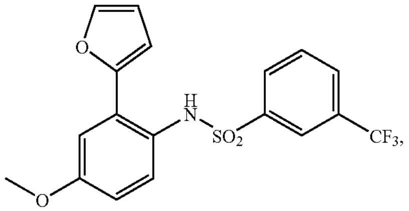

,

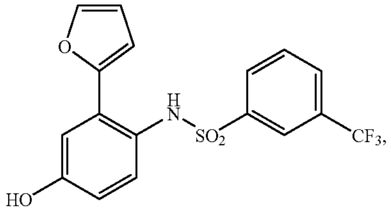

,

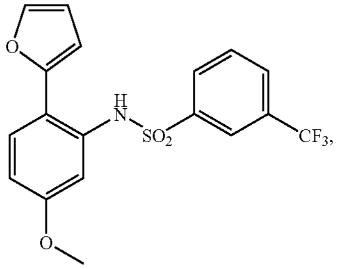

,

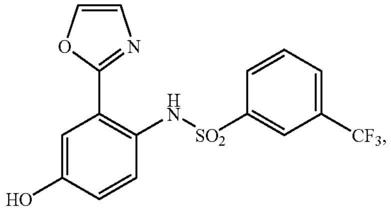

and

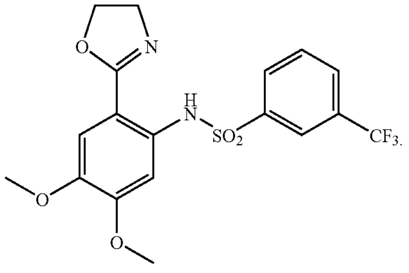

.

7. A pharmaceutical formulation comprising a pharmaceutically acceptable excipient and a compound having the formula:

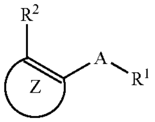

wherein ring system Z is a member selected from the group consisting of substituted or unsubstituted aryl, and substituted or unsubstituted $C_5$–$C_7$ carbocycle;

A is a member selected from —$NHS(O)_2$—, —$S(O)_2$ NH—, —$C(R^4R^5)S(O)_n$—, —$S(O)_nC(R^4R^5)$—, —$C(R^4R^5)NHS(O)_n$—, —$S(O)_nNHC(R^4R^5)$—, —$C(R^4R^5)S(O)_nNH$—, and —$HNS(O)_nC(R^4R^5)$— wherein n is selected from the integers from 0 to 2;

$R^1$ is a member selected from the group of substituted or unsubstituted aryl, and substituted or unsubstituted ($C_5$–$C^7$)carbocycle;

$R^2$ is a member selected from substituted or unsubstituted 2-furan, substituted or unsubstituted 2-thiazole and

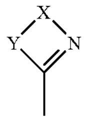

wherein

X is selected from the group consisting of —N═N—, —N═$C(R^4)$—, —$C(R^4)$═N—, —$C(R^4R^5)$—C ($R^4R^5$)— and —$C(R^4)$═$C(R^5)$—, wherein $R^4$ and $R^5$ are members independently selected from the group consisting of hydrogen, substituted and unsubstituted lower alkyl, —$OR^6$ and —$CF_3$ wherein $R^6$ is a member selected from hydrogen, and substituted or unsubstituted lower alkyl;

Y is O.

8. A pharmaceutical formulation comprising a pharmaceutically acceptable excipient and a compound according to claim 6.

* * * * *